(12) United States Patent
Lewis

(10) Patent No.: US 12,071,301 B2
(45) Date of Patent: Aug. 27, 2024

(54) APPARATUS FOR FACILITATING REFILLING OF MEDICATION INTO A PROGRAMMABLE MEDICATION DISPENSER

(71) Applicant: Victor Lewis, Royal Palm Beach, FL (US)

(72) Inventor: Victor Lewis, Royal Palm Beach, FL (US)

( * ) Notice: Subject to any disclaimer, the term of this patent is extended or adjusted under 35 U.S.C. 154(b) by 38 days.

(21) Appl. No.: 17/519,235

(22) Filed: Nov. 4, 2021

(65) Prior Publication Data

US 2022/0055833 A1  Feb. 24, 2022

Related U.S. Application Data

(63) Continuation-in-part of application No. 16/543,827, filed on Aug. 19, 2019, now Pat. No. 11,166,880, which is a continuation-in-part of application No. 15/539,038, filed on May 11, 2017, now Pat. No. 10,420,707.

(60) Provisional application No. 62/334,859, filed on May 11, 2016, provisional application No. 62/426,687, filed on Nov. 28, 2016.

(51) Int. Cl.
| | |
|---|---|
| *B65G 1/04* | (2006.01) |
| *A61J 7/00* | (2006.01) |
| *B65G 47/51* | (2006.01) |
| *B65G 47/82* | (2006.01) |

(52) U.S. Cl.
CPC .............. *B65G 1/04* (2013.01); *A61J 7/0084* (2013.01); *B65G 47/5195* (2013.01); *B65G 47/82* (2013.01); *B65G 2201/027* (2013.01); *B65G 2201/047* (2013.01)

(58) Field of Classification Search
CPC ................ B65G 1/04; B65G 2201/027; B65G 47/5195; B65G 47/82; B65G 2201/047; A61J 7/0084
See application file for complete search history.

(56) References Cited

U.S. PATENT DOCUMENTS

| | | | |
|---|---|---|---|
| 6,581,356 B2 * | 6/2003 | Kim ........................ | G07F 11/62 221/124 |
| 6,779,663 B1 * | 8/2004 | Pocsi ........................ | A61J 1/03 141/242 |
| 7,584,849 B2 * | 9/2009 | Mauk ................. | B65D 83/0445 206/459.1 |

(Continued)

*Primary Examiner* — Michael Collins

(57) ABSTRACT

Disclosed herein is an apparatus for facilitating refilling of medication into a programmable medication dispenser, in accordance with some embodiments. Further, the apparatus may include an apparatus body, a bottomless tray, a cover, a refilling actuator, and a power source. Further, the bottomless tray is configured to be movably disposed within a body interior space of the apparatus body. Further, compartments of the bottomless tray comprise a medication. Further, the cover is removably attached to a side of the bottomless tray for securing the medication in the compartments. Further, the refilling actuator is configured for displacing the bottomless tray from a storage position to a dispensing position within the body interior space. Further, the bottomless tray is dispensable through a body opening of the apparatus body in the dispensing position. Further, the power source is configured for powering the refilling actuator.

18 Claims, 41 Drawing Sheets

(56) References Cited

U.S. PATENT DOCUMENTS

| | | | | |
|---|---|---|---|---|
| 7,726,095 B2* | 6/2010 | Yuyama | ................... | B65B 5/103 |
| | | | | 221/253 |
| 7,922,037 B2* | 4/2011 | Ohmura | ................. | G06V 20/66 |
| | | | | 221/3 |
| 9,477,816 B2* | 10/2016 | Dent | ....................... | G16H 20/10 |
| 10,420,707 B2 | 9/2019 | Lewis | | |
| 10,593,145 B2* | 3/2020 | Patel | ..................... | G16H 20/13 |
| 2005/0240305 A1* | 10/2005 | Bogash | ..................... | A61J 7/04 |
| | | | | 700/242 |
| 2006/0058918 A1* | 3/2006 | Handfield | ............... | G07F 9/026 |
| | | | | 700/236 |
| 2007/0185615 A1* | 8/2007 | Bossi | .................... | A61J 7/0084 |
| | | | | 700/244 |
| 2009/0120042 A1* | 5/2009 | Zieher | .................... | B65B 35/06 |
| | | | | 53/494 |
| 2010/0106291 A1 | 4/2010 | Campbell | | |
| 2010/0318218 A1 | 12/2010 | Muncy | | |
| 2011/0215109 A1 | 9/2011 | Bailey | | |
| 2013/0030566 A1 | 1/2013 | Shavelsky | | |
| 2013/0197693 A1 | 8/2013 | Kamen | | |
| 2014/0172161 A1 | 6/2014 | Norris | | |
| 2014/0278508 A1 | 9/2014 | Akdogan | | |
| 2014/0297028 A1 | 10/2014 | Bilotti | | |
| 2015/0227127 A1 | 8/2015 | Miller | | |

* cited by examiner

APPARATUS FOR FACILITATING REFILLING OF MEDICATION INTO A PROGRAMMABLE MEDICATION DISPENSER The current application is a continuation-in-part (CIP) application of a U.S. non-provisional application Ser. No. 15/593,038 filed on May 11, 2017. The U.S. non-provisional application Ser. No. 15/593,038 claims a priority to a U.S. provisional application Ser. No. 62/334,859 filed on May 11, 2016.

FIELD OF THE INVENTION

The present disclosure generally relates to article dispenser. More specifically to an apparatus for facilitating refilling of medication into a programmable medication dispenser.

BACKGROUND OF THE INVENTION

A medication error is defined as any preventable event that may cause or lead to inappropriate medication use or harm to a patient. Since 2000, the Food and Drug Administration (FDA) has received more than 95,000 reports of medication errors. FDA reviews reports that come to MedWatch, the agency's adverse event reporting program. Actual numbers are expected to be higher, as many incidents go unreported. According to some studies, 400,000 preventable drug-related errors occur in hospitals each year; 800,000 occur in long-term care settings, and 530,000 occur in outpatient Medicare clinics Further, for many patients, medications need to be tightly controlled. For example, if the medications include restricted or controlled medicines.

Moreover, there are many incidents of suicide by prescription drug overdose, medication theft, accidental misuse of medications, and the unauthorized use of someone else's medication. Of particular concern are increasing incidents of theft and diversion by hospital staff and pharmacies.

Therefore, automatic medication dispensers are used to dispense medicines. Howey the available dispensers only partially solve the problems. The available dispensers are not fully secure and tamper-proof; therefore, they are susceptible to forceful tampering with standard hand tools and light power tools. Further, some available dispensers are not able to accurately track, monitor, and remind the patients to medicate properly.

Furthermore, the automatic medication dispenser is a portable device with a limited capacity of pills in the sliding trays. Therefore, the automatic medication dispenser may require refilling.

Therefore, there is a need for improved apparatus for facilitating refilling of medication into a programmable medication dispenser.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

Disclosed herein is an apparatus for facilitating refilling of medication into a programmable medication dispenser, in accordance with some embodiments. Further, the apparatus may include an apparatus body, at least one bottomless tray, at least one cover, at least one refilling actuator, and at least one power source. Further, the apparatus body may include at least one body wall and at least one body interior space formed by the at least one body wall. Further, the at least one body wall may include at least one body opening leading into the at least one body interior space. Further, the at least one bottomless tray may be configured to be movably disposed within the at least one body interior space. Further, the at least one bottomless tray may include a plurality of compartments. Further, each compartment of the plurality of compartments may include at least one compartment opening and at least one compartment wall forming a corresponding compartment. Further, the plurality of compartments may include at least one medication. Further, the at least one cover may be removably attached to at least one side of the at least one bottomless tray for securing the at least one medication in the plurality of compartments. Further, the at least one refilling actuator may be coupled with the at least one bottomless tray. Further, the at least one refilling actuator may be configured for displacing the at least one bottomless tray from at least one storage position to a dispensing position within the at least one body interior space. Further, the at least one bottomless tray may be dispensable through the at least one body opening in the dispensing position. Further, the at least one bottomless tray may not be dispensable through the at least one body opening in the at least one storage position. Further, the programmable medication dispenser receives the at least one bottomless tray through the at least one body opening based on dispensing of the at least one bottomless tray through the at least one body opening. Further, at least one power source may be coupled with the at least one refilling actuator. Further, the at least one power source may be configured for powering the at least one refilling actuator.

Further, disclosed herein is an apparatus for facilitating refilling of medication into a programmable medication dispenser, in accordance with some embodiments. Further, the apparatus may include an apparatus body, at least one bottomless tray, at least one cover, at least one refilling actuator, at least one power source, and at least one dispensing actuator. Further, the apparatus body may include at least one body wall and at least one body interior space formed by the at least one body wall. Further, the at least one body wall may include at least one body opening leading into the at least one body interior space. Further, the at least one bottomless tray may be configured to be movably disposed within the at least one body interior space. Further, the at least one bottomless tray may include a plurality of compartments. Further, each compartment of the plurality of compartments may include at least one compartment opening and at least one compartment wall forming a corresponding compartment. Further, the plurality of compartments may include at least one medication. Further, the at least one cover may be removably attached to at least one side of the at least one bottomless tray for securing the at least one medication in the plurality of compartments. Further, the at least one refilling actuator may be coupled with the at least one bottomless tray. Further, the at least one refilling actuator may be configured for displacing the at least one bottomless tray from at least one storage position to a dispensing position within the at least one body interior space. Further, the at least one bottomless tray may be dispensable through the at least one body opening in the dispensing position. Further, the at least one bottomless tray may not be dispensable through the at least one body opening in the at least one storage position. Further, the programmable medication dispenser receives the at least one bottomless tray through the at least one body opening based on dispensing of the at least one bottomless tray through the at least one body opening. Further, at least one power source may be coupled with the at least one refilling actuator. Further, the at least one power source may be configured for powering the at least one refilling actuator. Further, the at least one dispensing actuator may be coupled with the at least one bottomless tray. Further, the at least one dispensing actuator may be configured for moving the at least one bottomless tray in the dispensing position out of the apparatus body through the at least one body opening. Further, the at least one power source may be coupled with the at least one dispensing actuator. Further, the at least one power source may be configured for powering the at least one dispensing actuator.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and sub-combinations described in the detailed description.

BRIEF DESCRIPTION OF DRAWINGS

The accompanying drawings, which are incorporated in and constitute a part of this disclosure, illustrate various embodiments of the present disclosure. The drawings contain representations of various trademarks and copyrights owned by the Applicants. In addition, the drawings may contain other marks owned by third parties and are being used for illustrative purposes only. All rights to various trademarks and copyrights represented herein, except those belonging to their respective owners, are vested in and the property of the applicants. The applicants retain and reserve all rights in their trademarks and copyrights included herein, and grant permission to reproduce the material only in connection with reproduction of the granted patent and for no other purpose.

Furthermore, the drawings may contain text or captions that may explain certain embodiments of the present disclosure. This text is included for illustrative, non-limiting, explanatory purposes of certain embodiments detailed in the present disclosure.

DETAILED DESCRIPTION OF THE DRAWINGS

Figure 1:
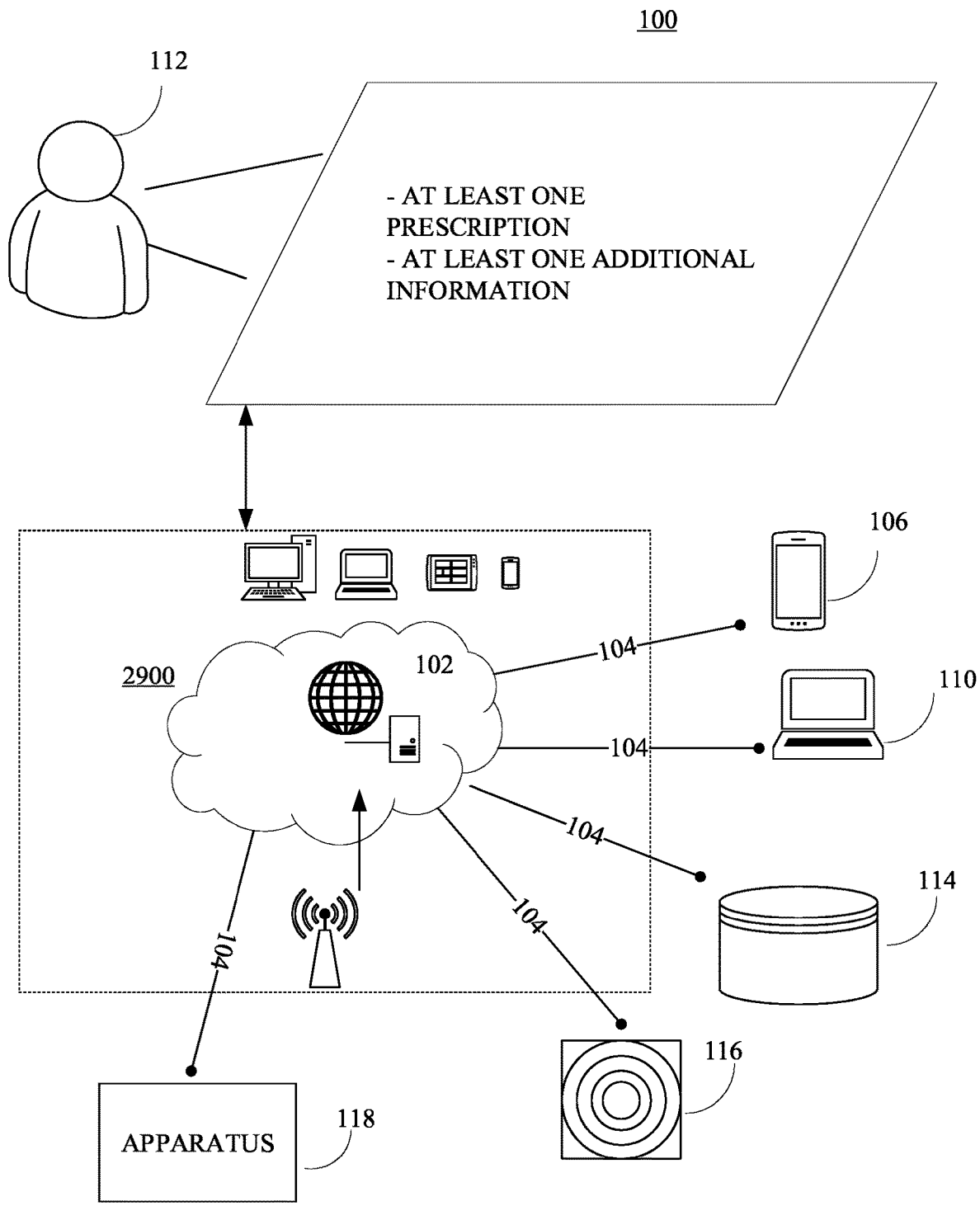
FIG. 1 is an illustration of an online platform consistent with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made merely for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim limitation found herein and/or issuing here from that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the disclosure. Instead, the proper scope of the disclosure is defined by the claims found herein and/or issuing here from. The present disclosure contains headers. It should be understood that these headers are used as references and are not to be construed as limiting upon the subjected matter disclosed under the header.

The present disclosure includes many aspects and features. Moreover, while many aspects and features relate to, and are described in the context of an apparatus for facilitating refilling of medication into a programmable medication dispenser, embodiments of the present disclosure are not limited to use only in this context.

In general, the method disclosed herein may be performed by one or more computing devices. For example, in some embodiments, the method may be performed by a server computer in communication with one or more client devices over a communication network such as, for example, the Internet. In some other embodiments, the method may be performed by one or more of at least one server computer, at least one client device, at least one network device, at least one sensor, and at least one actuator. Examples of the one or more client devices and/or the server computer may include, a desktop computer, a laptop computer, a tablet computer, a personal digital assistant, a portable electronic device, a wearable computer, a smartphone, an Internet of Things (IoT) device, a smart electrical appliance, a video game console, a rack server, a super-computer, a mainframe computer, mini-computer, micro-computer, a storage server, an application server (e.g. a mail server, a web server, a real-time communication server, an FTP server, a virtual server, a proxy server, a DNS server etc.), a quantum computer, and so on. Further, one or more client devices and/or the server computer may be configured for executing a software application such as, for example, but not limited to, an operating system (e.g. Windows, Mac OS, Unix, Linux, Android, etc.) in order to provide a user interface (e.g. GUI, touch-screen based interface, voice-based interface, gesture-based interface etc.) for use by the one or more users and/or a network interface for communicating with other devices over a communication network. Accordingly, the server computer may include a processing device configured for performing data processing tasks such as, for example, but not limited to, analyzing, identifying, determining, generating, transforming, calculating, computing, compressing, decompressing, encrypting, decrypting, scrambling, splitting, merging, interpolating, extrapolating, redacting, anonymizing, encoding and decoding. Further, the server computer may include a communication device configured for communicating with one or more external devices. The one or more external devices may include, for example, but are not limited to, a client device, a third-party database, public database, a private database and so on. Further, the communication device may be configured for communicating with the one or more external devices over one or more communication channels. Further, the one or more communication channels may include a wireless communication channel and/or a wired communication channel. Accordingly, the communication device may be configured for performing one or more of transmitting and receiving of information in electronic form. Further, the server computer may include a storage device configured for performing data storage and/or data retrieval operations. In general, the storage device may be configured for providing reliable storage of digital information. Accordingly, in some embodiments, the storage device may be based on technologies such as, but not limited to, data compression, data backup, data redundancy, deduplication, error correction, data fingerprinting, role-based access control, and so on.

Further, one or more steps of the method disclosed herein may be initiated, maintained, controlled and/or terminated based on a control input received from one or more devices operated by one or more users such as, for example, but not limited to, an end-user, an admin, a service provider, a service consumer, an agent, a broker and a representative thereof. Further, the user as defined herein may refer to a human, an animal or an artificially intelligent being in any state of existence, unless stated otherwise, elsewhere in the present disclosure. Further, in some embodiments, the one or more users may be required to successfully perform authentication in order for the control input to be effective. In general, a user of the one or more users may perform authentication based on the possession of a secret human-readable secret data (e.g. username, password, passphrase, PIN, secret question, secret answer etc.) and/or possession of a machine-readable secret data (e.g. encryption key, decryption key, bar codes, etc.) and/or possession of one or more embodied characteristics unique to the user (e.g. biometric variables such as, but not limited to, fingerprint, palm-print, voice characteristics, behavioral characteristics, facial features, iris pattern, heart rate variability, evoked potentials, brain waves, and so on) and/or possession of a unique device (e.g. a device with a unique physical and/or chemical and/or biological characteristic, a hardware device with a unique serial number, a network device with a unique IP/MAC address, a telephone with a unique phone number, a smart-card with an authentication token stored thereupon, etc.). Accordingly, the one or more steps of the method may include communicating (e.g. transmitting and/or receiving) with one or more sensor devices and/or one or more actuators in order to perform authentication. For example, the one or more steps may include receiving, using the communication device, the secret human-readable data from an input device such as, for example, a keyboard, a keypad, a touch-screen, a microphone, a camera and so on. Likewise, the one or more steps may include receiving, using the communication device, the one or more embodied characteristics from one or more biometric sensors.

Further, one or more steps of the method may be automatically initiated, maintained and/or terminated based on one or more predefined conditions. In an instance, the one or more predefined conditions may be based on one or more contextual variables. In general, the one or more contextual variables may represent a condition relevant to the performance of the one or more steps of the method. The one or more contextual variables may include, for example, but are not limited to, location, time, identity of a user associated with a device (e.g. the server computer, a client device etc.) corresponding to the performance of the one or more steps, environmental variables (e.g. temperature, humidity, pressure, wind speed, lighting, sound, etc.) associated with a device corresponding to the performance of the one or more steps, physical state and/or physiological state and/or psychological state of the user, physical state (e.g. motion, direction of motion, orientation, speed, velocity, acceleration, trajectory, etc.) of the device corresponding to the performance of the one or more steps and/or semantic content of data associated with the one or more users. Accordingly, the one or more steps may include communicating with one or more sensors and/or one or more actuators associated with the one or more contextual variables. For example, the one or more sensors may include, but are not limited to, a timing device (e.g. a real-time clock), a location sensor (e.g. a GPS receiver, a GLONASS receiver, an indoor location sensor etc.), a biometric sensor (e.g. a fingerprint sensor), an environmental variable sensor (e.g. temperature sensor, humidity sensor, pressure sensor, etc.) and a device state sensor (e.g. a power sensor, a voltage/current sensor, a switch-state sensor, a usage sensor, etc. associated with the device corresponding to performance of the or more steps).

Further, the one or more steps of the method may be performed one or more number of times. Additionally, the one or more steps may be performed in any order other than as exemplarily disclosed herein, unless explicitly stated otherwise, elsewhere in the present disclosure. Further, two or more steps of the one or more steps may, in some embodiments, be simultaneously performed, at least in part. Further, in some embodiments, there may be one or more time gaps between performance of any two steps of the one or more steps.

Further, in some embodiments, the one or more predefined conditions may be specified by the one or more users. Accordingly, the one or more steps may include receiving, using the communication device, the one or more predefined conditions from one or more and devices operated by the one or more users. Further, the one or more predefined conditions may be stored in the storage device. Alternatively, and/or additionally, in some embodiments, the one or more predefined conditions may be automatically determined, using the processing device, based on historical data corresponding to performance of the one or more steps. For example, the historical data may be collected, using the storage device, from a plurality of instances of performance of the method. Such historical data may include performance actions (e.g. initiating, maintaining, interrupting, terminating, etc.) of the one or more steps and/or the one or more contextual variables associated therewith. Further, machine learning may be performed on the historical data in order to determine the one or more predefined conditions. For instance, machine learning on the historical data may determine a correlation between one or more contextual variables and performance of the one or more steps of the method. Accordingly, the one or more predefined conditions may be generated, using the processing device, based on the correlation.

Further, one or more steps of the method may be performed at one or more spatial locations. For instance, the method may be performed by a plurality of devices interconnected through a communication network. Accordingly, in an example, one or more steps of the method may be performed by a server computer. Similarly, one or more steps of the method may be performed by a client computer. Likewise, one or more steps of the method may be performed by an intermediate entity such as, for example, a proxy server. For instance, one or more steps of the method may be performed in a distributed fashion across the plurality of devices in order to meet one or more objectives. For example, one objective may be to provide load balancing between two or more devices. Another objective may be to restrict a location of one or more of an input data, an output data and any intermediate data therebetween corresponding to one or more steps of the method. For example, in a client-server environment, sensitive data corresponding to a user may not be allowed to be transmitted to the server computer. Accordingly, one or more steps of the method operating on the sensitive data and/or a derivative thereof may be performed at the client device.

Overview:

The present disclosure describes an apparatus for facilitating refilling of medication into a programmable medication dispenser (Pill-Lockers). Further, the programmable medication dispenser may be at least one of a portable, a secured and an automated dispenser for prescription medications. Further, the programmable medication dispenser may prevent patients from accidentally or deliberately abusing medications. Further, the programmable medication dispenser may remind the patients to take the medications at the prescribed time.

Further, the programmable medication dispenser may include a plurality of sizes, shapes, and colors. Further, the programmable medication dispenser may be configured for any application or any medication prescribed to the patients.

Further, the programmable medication dispenser may include a micro-controller. Further, the micro-controller may be capable of operating up to 100 trays over a 10-year prescription duration. Further, the microcontroller may be programmed using a smartphone, a laptop, etc. using a Bluetooth, a USB, or an RS232 connection. Further, the programmable medication dispenser may include a plurality of options. Further, the options may include LED Readout, speech, encapsulation, and network and cloud software compatibility.

Further, the programmable medication dispenser may include a drive motor. Further, the drive motor may include a custom-designed stepper motor. Further, the custom-designed stepper motor may be controlled by the microcontroller to provide the instant and precise "micro-motions" necessary for accurate dispensing of medication.

Further, the programmable medication dispenser may include a dispenser drive. Further, the dispenser drive may include custom die-rolled stainless-steel drive screws and a stainless-steel micro-bearing technology. Further, parts of the dispenser drive may include stainless steel, sintered Aluminum alloy, brass, and nylon.

Further, the programmable medication dispenser may include medication trays. Further, the medication trays may be interchangeable and disposable. Further, the medication trays may include Food and Drug Administration (FDA) approved food grade plastic, acrylic, or stainless steel. Further, the medication trays may be easily removed for cleaning or replacement. Further, the programmable medication dispenser may be configured with a plurality of sizes of the medication trays having individual cells configured to match pill and capsule shapes and dosage frequency. Further, the medication trays may be prepackaged with the medications by at least one of manufacturers, in-house pharmacies, and compounding pharmacies.

Further, the programmable medication dispenser may include a secure enclosure. Further, the secure enclosure may include at least one of plastic, acrylic, aluminum, cast alloy, and stainless steel. Further, the at least one of plastic, acrylic, aluminum, cast alloy, and stainless steel may allow for different levels of security. Further, the programmable medication dispenser may include a "Medication Self-Destruct" option. Further, the programmable medication dispenser may be designed to be disassembled and sterilized using temperature and/or chemical gas. Further, the programmable medication dispenser may have food grade Teflon floors that may be removed by a user for cleaning. Further, manufacturers and agencies may handle possession of the programmable medication dispenser. Further, the manufacturers and the agencies may rent and lease the programmable medication dispenser to the user. Further, the programmable medication dispenser may be upgraded, refurbished, re-programmed, and re-purposed.

Further, the programmable medication dispenser may include a patient-accessible compartment for one or two "emergency doses" of the medication in the case of any failure to dispense the medications. Further, the programmable medication dispenser may provide assistance through a local pharmacy.

Further, the programmable medication dispenser may immediately end overuse, illegal Sale, and "Gifting" of dangerous medications.

Further, the programmable medication dispenser may prevent overdose. Further, the programmable medication dispenser may dispense the medications based on a prescription provided by at least one physician. Further, the programmable medication dispenser may dispense the medications on a time prescribed in the prescription.

Further, the programmable medication dispenser may be completely tamper-proof. Further, the programmable medication dispenser may include an internal system that may neutralize the medications if an external shield may be breached. Further, in a case of theft, a global positioning system (GPS) included in the programmable medication dispenser may record and transmit the location of the programmable medication dispenser.

Further, the present disclosure describes the apparatus (refill dispenser) for facilitating the refilling of the medication into the programmable medication dispenser (pill-locker) allows allow patients to refill their Pill-Locker but still maintain security dispense control, the Refill Dispenser has linked Bluetooth technology to the Pill-Locker to track the prescription and to know when the Pill-Locker will require a reload. The apparatus may be secured in the home medicine cabinet or other location for easy access. A removable battery pack/charger that plugs directly into a USB charger or a home electrical outlet to charge and then plug directly into the Pill-Locker to operate the dispensing process. The trays are pre-filled and a removable cellophane peel-off cover keeps the pills in place.

Further, the apparatus may include a monitor and a battery pack with a key lock. Further, the apparatus may include an internal Bluetooth stepper lock. Further, the apparatus may include one or more pre-filled trays hanging on rods with a "pusher" driven by a drive screw. Further, the trays are hung on a rod with the pusher driven by a stepper motor controlled by a Bluetooth processor board. As the tray is pushed forward, it travels up a ramp and drops out an opening at the bottom of the apparatus. The ramp then moves forward sealing the opening to prevent tampering.

Further, the refilling of the pill-locker by the apparatus may include a loading of the Pill-Locker with trays removed into the apparatus (loader). Automatic commands verify prescription. Further, the Lock Motor lowers the wedge for the Pill-Locker to be inserted. Once inserted, the Lock Motor extends a deadbolt wedge into the Pill-Locker to prevent removal during the loading process. Lifter Motor raises the lifter to sensor aligning to front opening of Pill-Locker. Once aligned, Push Motor advances a number of trays a short, calibrated distance over the Pill-Locker drive nut. Once the trays nut opening is aligned, the lifter lowers for the opening to seat over the nut. The Pill-Locker then draws in the trays. When the trays are fully drawn into the Pill-Locker, The Lock motor withdraws the wedge, and the Pill-Locker can be removed.

FIG. 1 is an illustration of an online platform 100 consistent with various embodiments of the present disclosure. By way of non-limiting example, the online platform 100 to facilitate operations of an apparatus for facilitating refilling of medication into a programmable medication dispenser may be hosted on a centralized server 102, such as, for example, a cloud computing service. The centralized server 102 may communicate with other network entities, such as, for example, a mobile device 106 (such as a smartphone, a laptop, a tablet computer, etc.), other electronic devices 110 (such as desktop computers, server computers etc.), databases 114, apparatus 118 (such as the apparatus 3000, the apparatus 4100, etc.) and sensors 116 over a communication network 104, such as, but not limited to, the Internet. Further, users of the online platform 100 may include relevant parties such as, but not limited to, end-users, administrators, service providers, service consumers and so on. Accordingly, in some instances, electronic devices operated by the one or more relevant parties may be in communication with the platform.

A user 112, such as the one or more relevant parties, may access online platform 100 through a web-based software application or browser. The web-based software application may be embodied as, for example, but not be limited to, a website, a web application, a desktop application, and a mobile application compatible with a computing device 2900.

Further, the user 112 may be able to program the programmable medication dispenser. Further, the user may program the dispensing of at least one medication by the programmable medication dispenser.

Figure 2:
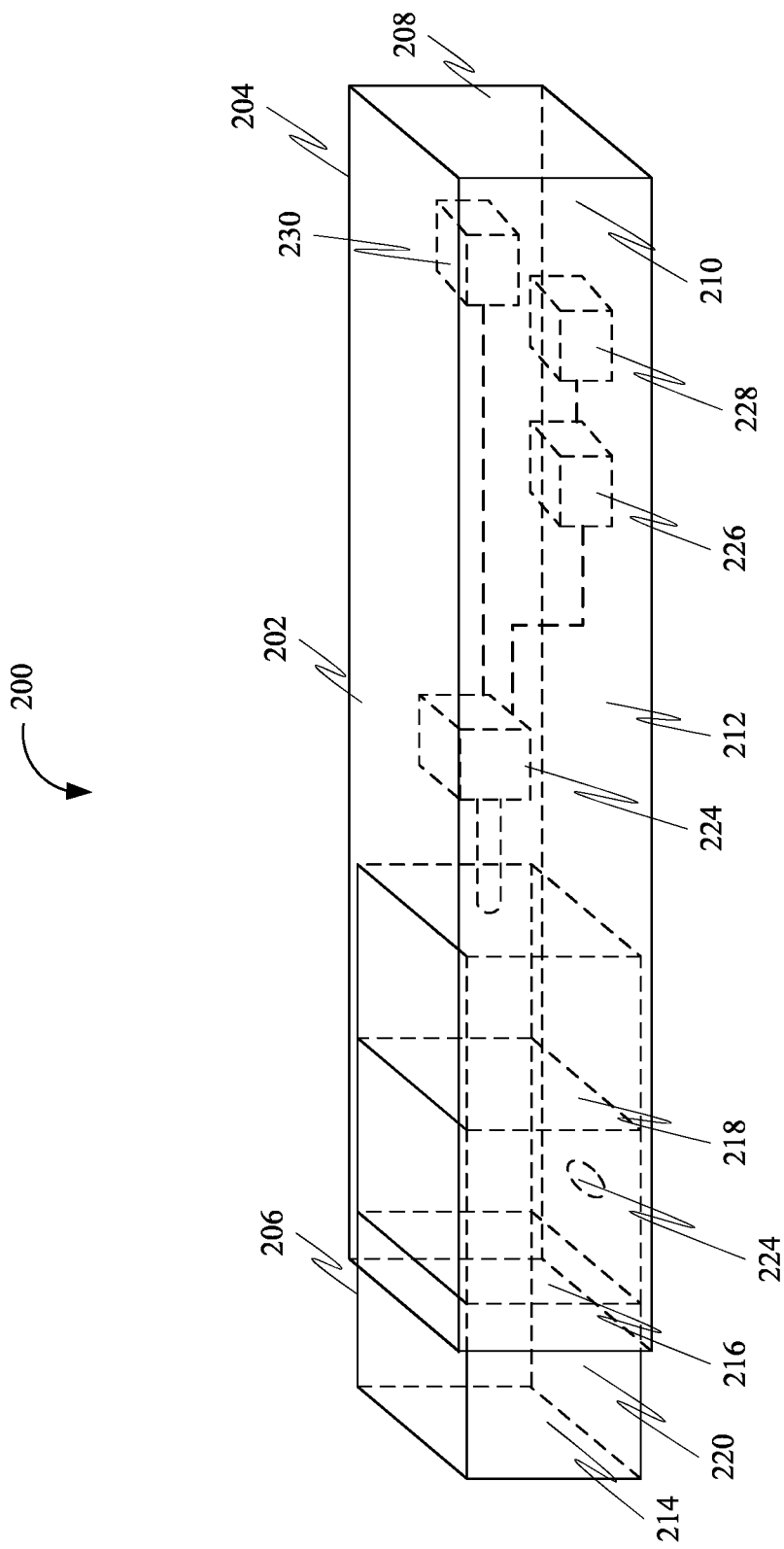
FIG. 2 is a front view of a programmable medication dispenser, in accordance with some embodiments.

FIG. 2 is a front view of a programmable medication dispenser 200, in accordance with some embodiments. Further, the programmable medication dispenser 200 may include a housing 202, a base wall 212, at least one actuator 224, at least one power source 230, a processing device 226 and a storage device 228. Further, the programmable medication dispenser 200 may be disposed on at least one treatment site. Further, the at least one treatment site may include cabinet, bedpost, etc.

Further, the housing 202 may include a body 204 and at least one bottomless tray 206.

Further, the body 204 may include at least one wall 208-210 and at least one interior space formed by the at least one wall 208-210. Further, the interior space formed by the at least one wall 208-210 may include a plurality spatial configurations. Further, the plurality of spatial configurations may include tetrahedral configurations, cuboidal configurations, spherical configurations, and so on. Further, in an instance, the housing 202 may be shaped as a disc.

Further, the at least one bottomless tray 206 configured to be movably disposed within the at least one interior space. Further, the bottomless tray 206, in an instance, may be removed by at least one user. Further, the at least one bottomless tray 206 may include a plurality of compartments 214-218. Further, each compartment may include at least one compartment opening 220 and at least one compartment wall forming a corresponding compartment. Further, the bottomless tray 206, in an instance, may include the plurality of compartments 214-218. Further, each compartment of the plurality of compartments 214-218 may include two compartment openings 220 placed opposite to the each of the compartment opening 220 of the two compartment openings 220.

Further, the bottomless tray 206, in an instance, may include the plurality of compartments 214-218. Further, the each compartment of the plurality of compartments 214-218 may include one compartment opening 220.

Further, in an embodiment, the housing 202 further may include at least one collection unit. Further, the at least one collection unit may include at least one collection wall and a collection space formed by the at least one collection wall. Further, the at least one collection unit may include at least one collection opening contiguous with at least one aperture 222 in order to collect the at least one medication through the at least one aperture 222 of the base wall 212. Further, the collection space may be externally accessible. Further, the at least one medication may include at least one pill, at least one capsule, at least one vial, and so on.

Further, in an embodiment, the housing 202 further may include at least one emergency unit. Further, the at least one emergency unit may be disposed in the body 204 of the housing 202. Further, the at least one emergency unit may include at least one emergency unit wall and an emergency unit space formed by the at least one emergency unit wall. Further, the at least one emergency unit may include an emergency unit aperture in the at least one emergency unit wall. Further, the emergency unit space may be configured to accommodate an emergency medication. Further, the emergency unit space may be externally accessible independent of a state of the at least one actuator 224.

Further, in an embodiment, the housing 202 may include a tamper-proof material. Further, the tamper-proof material may include at least one of stainless steel, a metal alloy, a high strength acrylic laminate, and a composite plastic. Further, the tamper-proof material may ensure the safety of the housing 202 and the at least one medication included in the housing 202.

Further, in an embodiment, the at least one bottomless tray 206 may include of at least one of chemical-resistant plastic, chemical-resistant acrylic, and chemical-resistant stainless steel. Further, the at least one of the chemical-resistant plastic, the chemical-resistant acrylic, and the chemical-resistant stainless steel may not chemically contaminate the at least one medication disposed on the at least one bottomless tray 206

Further, the base wall 212 disposed on one side of the at least one bottomless tray 206. Further, the base wall 212 may include the at least one aperture 222 corresponding to the at least one bottomless tray 206. Further, the at least one aperture 222 may include a plurality of planar configurations. Further, the plurality of planar configurations may include triangular configurations, quadrilateral configurations, circular configurations, and so on. Further, an aperture of the at least one aperture 222 corresponding to a bottomless tray 206 of the at least one bottomless tray 206 may be configured to receive at least one medication included in a compartment of the plurality of compartments 214-218 of the bottomless tray 206 upon displacement of the bottomless tray 206 in relation to the base wall 212 such that the at least one compartment opening 220 of the compartment overlaps at least partially with the at least one aperture 222. Further, the at least one bottomless tray 206 may include the plurality of spatial configurations. Further, the plurality of compartments may include the plurality of spatial configurations.

Further, in an embodiment, the base wall may be configured to be movably disposed. Further, the base wall 212 may be configured to be displaced in relation to the at least one bottomless tray 206 through a plurality of base wall positions. Further, the at least one aperture 222 may include a plurality of apertures corresponding to a plurality of sizes corresponding to the plurality of base wall positions. Further, the base wall 212 being in a first position of the plurality of base wall positions, a first aperture of the plurality of apertures corresponding to the first position overlaps with the at least one compartment opening 220 of the plurality of compartments 214-218.

Further, in an embodiment, the base wall 212 may include of at least one of Teflon, Nylon, Acetal, and Polyester on at least on a side of the base wall 212 facing the at least compartment opening 220 of the plurality of compartments 214-218. Further, the at least one of Teflon, Nylon, Acetal, and Polyester may have a low coefficient of friction and may facilitate easy cleaning of the at least one base wall 212.

Further, in an embodiment, the at least one compartment wall of the plurality of compartments 214-218 may be coated with at least one of an abrasive and a vitreous material configured to perform at least one of abrade and deflect a drill-bit. Further, the at least one the abrasive and the vitreous material may prevent the forceful entry of the plurality of the compartments 214-218.

Further, the at least one actuator 224 coupled to the at least one bottomless tray 206. Further, the at least one actuator 224 may be configured to displace the at least one bottomless tray 206 through a plurality of positions in relation to the base wall 212. Further, the plurality of the positions may include a plurality of positions interior to the housing 202. Further, the plurality of positions may include a plurality of positions exterior to the housing 202.

Further, in an embodiment, the at least one actuator 224 may include at least one linear actuator. Further, a linear actuator of the at least one linear actuator may be configured to cause linear motion of a bottomless tray 206 of the at least one bottomless tray 206 in relation to the base wall 212. Further, the linear actuator may include a nut attached to the bottomless tray. Further, the nut may include internal threading. Further, the nut may be configured to accommodate a rod may include external threading. Further, the nut may be threadedly coupled with the rod such that rotation of the rod causes linear motion of the bottomless tray. Further, the rod may be rotatably coupled to a stepper motor through a gear assembly. Further, the gear assembly may include at least one gear rotatably coupled to a rotor of the stepper motor. In an alternate embodiment, the rod may be rotatably coupled to a stepper motor with no gears involved (that is, direct drive). Further, the at least one of the nut and the rod may include of at least one of die-rolled stainless steel, aluminum alloy, brass, and nylon. Further, the at least one of die-rolled stainless steel, aluminum alloy, brass, and nylon may ensure the strength and durability of the at least one of the nut and the rod. Further, the at least one actuator, in an instance may include at least one lead screw. Further, the at least one lead screw may be mounted on at least one bearing. Further, the at least one bearing may include nylon bearing, stainless steel bearing, etc. Alternatively, the at least one lead screw may be directly attached to the motor with no gears involved (that is, direct drive).

Further, the at least one power source 230 configured to provide power to the at least one actuator 224. Further, the at least one power source 230 may be removably disposed in the housing 202. Further, at least one power source 230 may be fixed in the housing 202. Further, the at least one power source 230, in an instance may include at least one direct current (DC) battery. Further, a DC battery of the at least one DC battery may provide constant voltage DC current to power the at least one actuator 224.

Further, the processing device 226 communicatively coupled to the at least one actuator 224. Further, the processing device 226 may be configured to control the at least one actuator 224 based on at least one data. Further, the at least one data may include a medication schedule data. Further, the medication schedule data may include name of the at least one medication, description of at least one medication, the dosage of at least one medication, name of at least one user, and so on. Further, the at least one user may include at least one patient, at least one doctor, at least one pharmacist, at least on care-giver, etc. Further, the processing device 226 may process the medication schedule data and based on processing the processing device 226 may control the at least one actuator 224 to initiate dispensing of the at least one medication.

Further, the storage device 228 communicatively coupled to the processing device 226. Further, the storage device 228 may be configured to store the at least one data. Further, the at least one data may include the medication data, user personal data, etc. Further, the storage device 228 may store the at least one data may be stored in a database.

Further, in some embodiments, the programmable medication dispenser 200 may further include at least one sensor communicatively coupled with the processing device 226. Further, the at least one sensor may be associated with the at least one bottomless tray 206. Further, the at least one sensor may be configured to generate at least one sensor data. Further, the at least one sensor data may be associated with the displacement of the at least one bottomless tray 206. Further, the displacement may be associated with the plurality of positions of the at least one bottomless tray 206.

Further, in some embodiments, the programmable medication dispenser 200 may further include at least one lock mechanism associated with the at least one bottomless tray 206. Further, at least one lock mechanism may be actuated using the at least one actuator 224. Further, a lock mechanism corresponding to a bottomless tray 206 may include at least one latch. Further, the latch may be configured to be in one of a locked state and an unlocked state. Further, in the locked state, the lock mechanism may be configured to prevent displacement of the bottomless tray 206. Further, in the unlocked state, the lock mechanism may be configured to allow displacement of the bottomless tray 206 facilitating dispensing of the at least one medication.

Further, in some embodiments, the programmable medication dispenser 200 may further include a communication device communicatively coupled with the processing device 226. Further, the communication device may be configured to perform at least one of receiving a receive data may include the at least one data from at least one user device and transmitting a transmit data to the at least one user device. Further, the at least one user device may be associated with at least one user. Further, the at least one user device may include computing devices such as, but not limited to, smartphones, smartwatches, tablets, personal computers (PC), desktops, laptops, and so on. Further, the at least one user may include patient, doctor, pharmacist, law authority, and so on. Further, the communication device may include at least one wireless transmitter and at least one wireless receiver. Further, the wireless transmitter, in an instance, may include, but not limited, but not limited to, a Wi-Fi, a Bluetooth, an electromagnetic waveform, ultra-sound, cellular (5G) and/or an Infra-red, etc. Further, the communication device may be remotely connected to the at least one user. Further, the receive data may include the medication schedule data, program data, and so on. Further, the program data may include a set of instruction that relates to at least one operation of the programmable medication dispenser 200. Further, the at least one operation may include dispensing of the at least one medication. Further, the transmit data may include status data, medication data, and so on. Further, the status data may include power levels of the DC battery. Further, the medication data may include a plurality of types of the at least one medication and quantity of the plurality of types of the at least one medication.

Further, in some embodiments, the programmable medication dispenser 200 may further include a tampering sensor (not shown) configured to detect at least one tampering action performed on the programmable medication dispenser 200. Further, the tampering sensor may be configured to detect the breaking of at least one compartment of the plurality of compartments 214-218. Further, the tampering sensor may be communicatively coupled to the processing device 226. Further, the processing device 226 may be configured to generate at least one tampering alert based on detection of the at least one tampering action. Further, the communication device may be configured to transmit the at least one tampering alert to at least one user device. Further, the at least one user device may be associated with the at least one user.

Further, in some embodiments, the programmable medication dispenser 200 may further include at least one chemical container and at least one chemical actuator. Further, the at least one chemical container may include a chemical agent. Further, the at least one chemical actuator coupled to the at least one chemical container. Further, the at least one chemical actuator may be configured to release the chemical agent into at least one compartment of the plurality of compartments 214-218 when the at least one chemical actuator may be activated. Further, the at least one chemical actuator may be communicatively coupled to the tampering sensor. Further, detection of the at least one tampering action causes activation of the at least one chemical actuator. Further, the chemical agent may be configured to react with a medication contained in the at least one compartment in order to render the medication unusable.

Further, in some embodiments, the programmable medication dispenser 200 may further include at least one chemical container and at least one chemical actuator. Further, the at least one chemical container may include a chemical agent. Further, the at least one chemical actuator coupled to the at least one chemical container. Further, the at least one chemical actuator may be configured to release the chemical agent into at least one compartment of the plurality of compartments 214-218 when the at least one chemical actuator may be activated. Further, the at least one chemical actuator may be communicatively coupled to the processing device 226. Further, the processing device 226 may be further configured to generate a chemical release command. Further, receipt of the chemical release command causes activation of the at least one chemical actuator.

Further, the programmable medication dispenser 200 may further include at least one positioning system. Further, the at least one positioning system may be communicatively coupled with the communication device. Further, the at least one positioning system may be configured to determine geographical location data of the programmable medication dispenser 200. Further, the geographical location data may include current geographical location of the programmable medication dispense 200, time, date, etc. Further, the at least one positioning system may include a global positioning system (GPS), a global satellite navigation system (GLO-NASS), and so on. Further, the communication device may be configured to transmit the geographical location data to the at least one user device. Further, the at least one user device may be associated with the at least one user.

Further, in an embodiment, the at least one user may perform the at least one management activity related to the programmable medication dispenser 200. Further, the at least one user may have access to the programmable medication dispenser 200. Further, the at least one management activity, in an instance, may include stocking at least one medication, cleaning at least one bottomless tray 206, etc.

Figure 3:
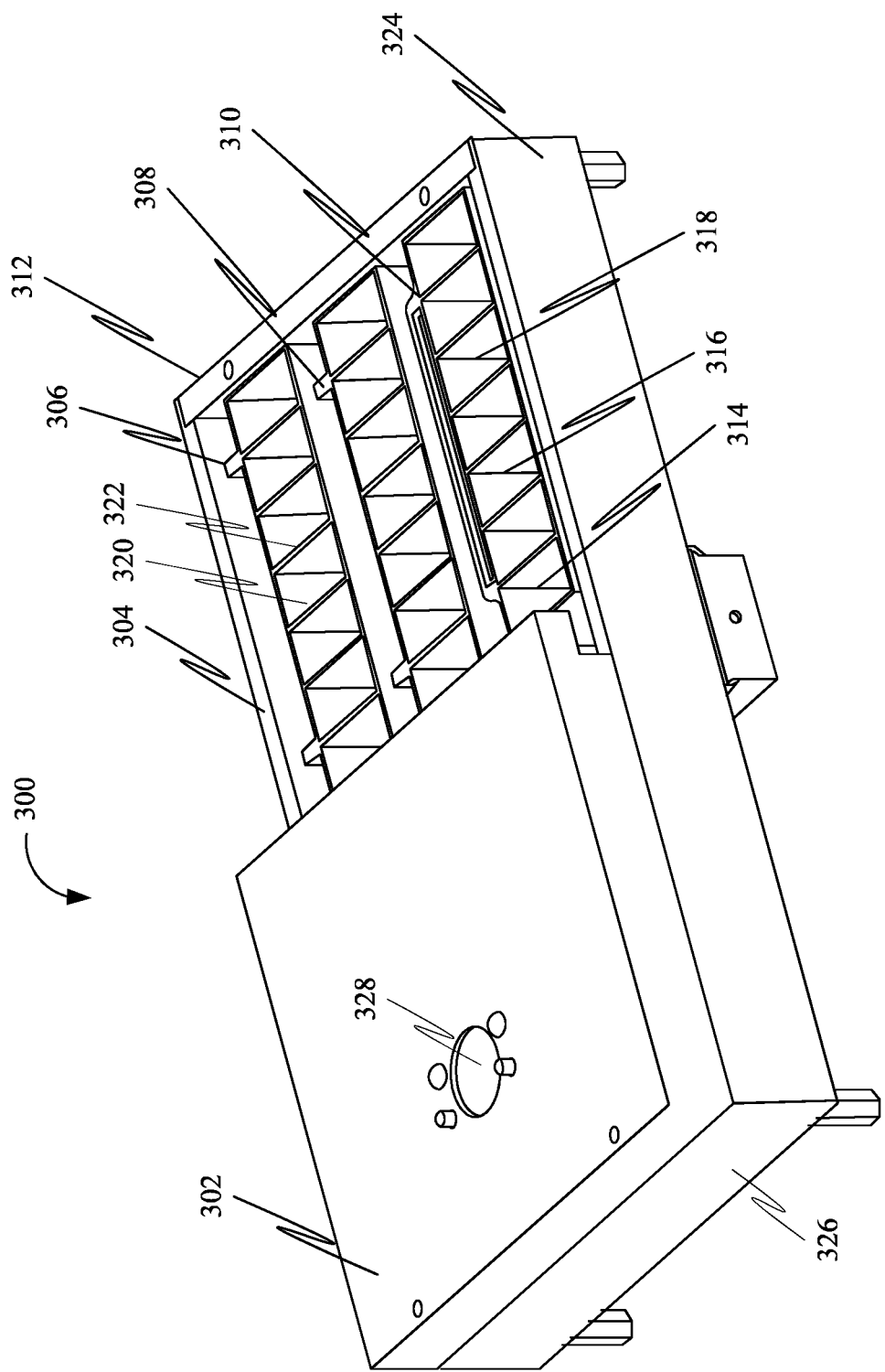
FIG. 3 is a front cross-sectional view of a programmable medication dispenser, in accordance with some embodiments.
Figure 4:
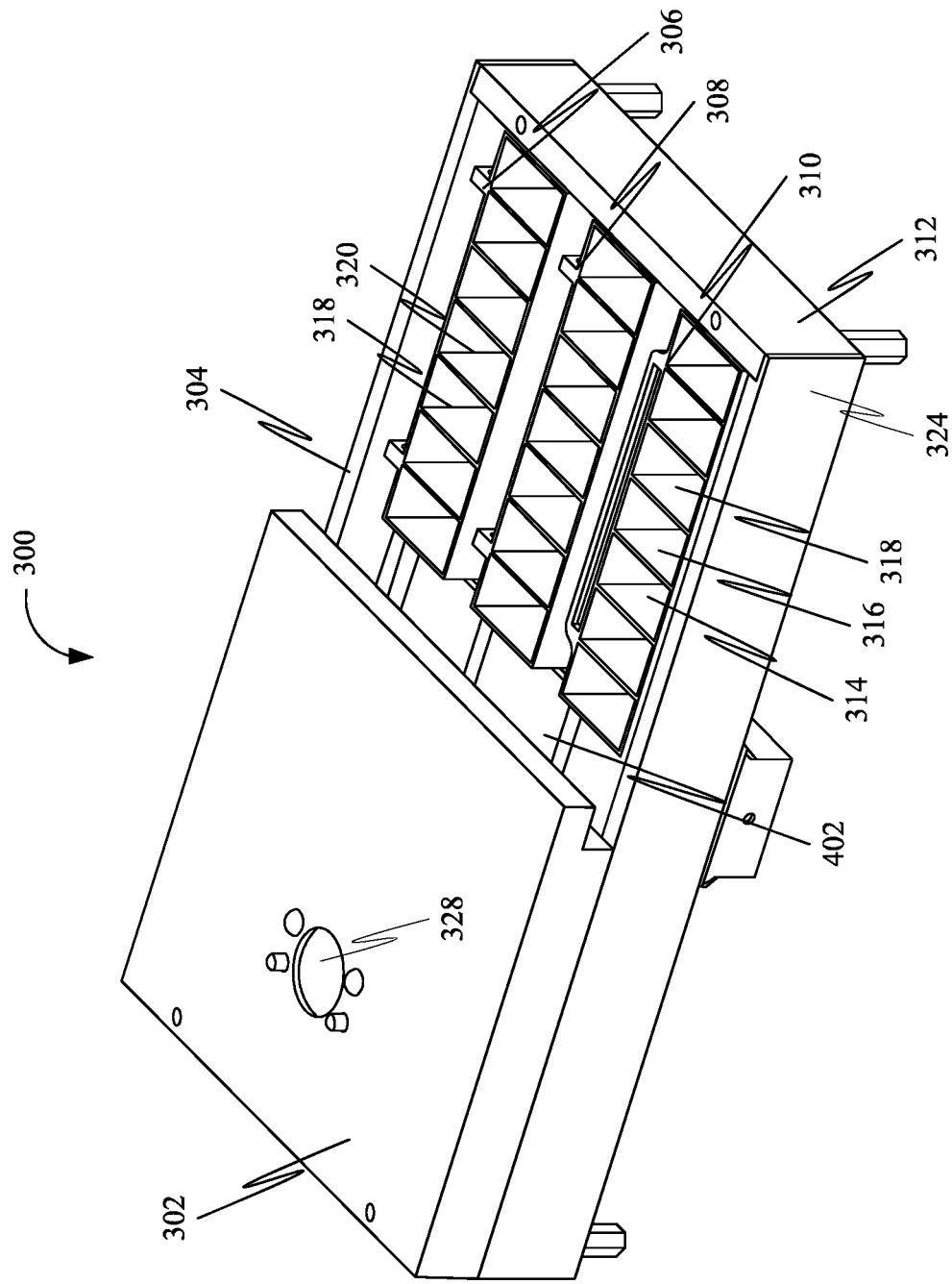
FIG. 4 is a front perspective cross-sectional view of a programmable medication dispenser, in accordance with some embodiments.

FIG. 3 is a front cross-sectional view of a programmable medication dispenser 300, in accordance with some embodiments. Further, the programmable medication dispenser may include a housing 302 (similar to the housing 202), at least one wall 312, 324-326 (similar to the at least one wall 208-210), at least one bottomless tray 306-310 (similar to the at least one bottomless tray 206), a plurality of compartments 318-322 (similar to the plurality of components 318-322), at least one compartment opening 314-316, power button 328, a base wall 402 (similar to the base wall 212) as shown in FIG. 4. Further, the power button 328 may activate the programmable medication dispenser 300.

FIG. 4 is a front perspective cross-sectional view of a programmable medication dispenser 300.

Figure 5:
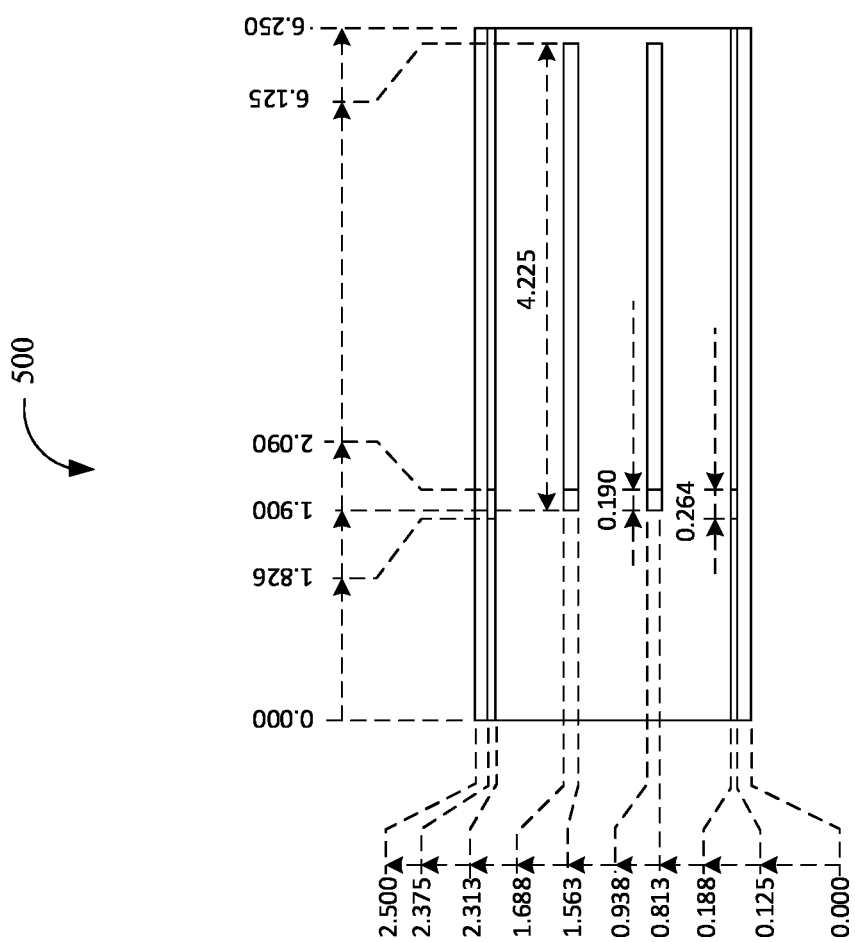
FIG. 5 is a front view of a base wall, in accordance with some embodiments.

FIG. 5 is a front view of a base wall 500 (similar to the base wall 212), in accordance with some embodiments. Further, the base wall 500 may include a plurality of components. Further, an exemplary dimension of the plurality of components may be indicated. Further, the unit of the exemplary dimension may be "inch".

Figure 6:
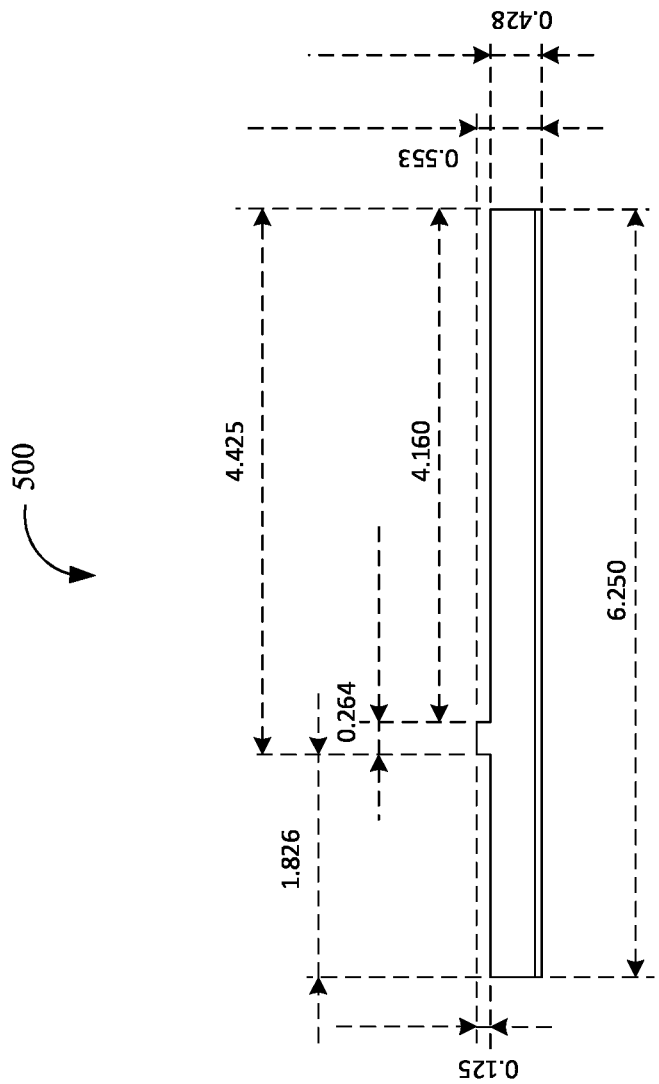
FIG. 6 is a side view of the base wall, in accordance with some embodiments.

FIG. 6 is a side view of the base wall 500 (similar to the base wall 212), in accordance with some embodiments. Further, the base wall 500 may include a plurality of components. Further, an exemplary dimension of the plurality of components may be indicated. Further, the unit of the exemplary dimension may be "inch".

Figure 7:
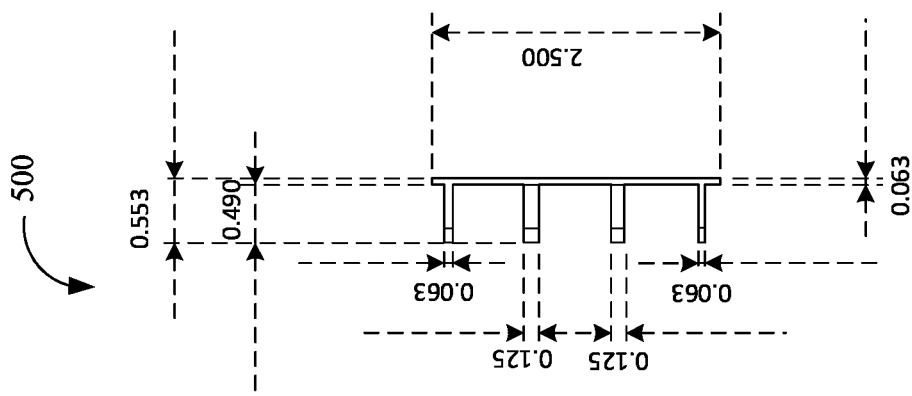
FIG. 7 is a top view of the base wall, in accordance with some embodiments

FIG. 7 is a top view of the base wall 500 (similar to the base wall 212), in accordance with some embodiments. Further, the base wall 500 may include a plurality of components. Further, an exemplary dimension of the plurality of components may be indicated. Further, the unit of the exemplary dimension may be "inch".

Figure 8:
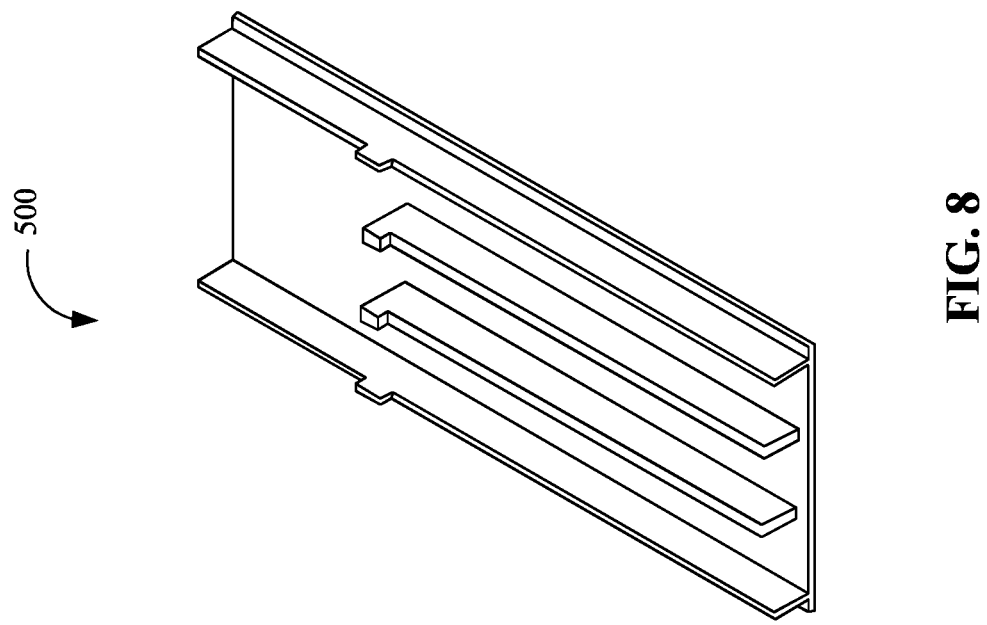
FIG. 8 is a front perspective view of the base wall, in accordance with some embodiments.

FIG. 8 is a front perspective view of the base wall 500 (similar to the base wall 212), in accordance with some embodiments.

Figure 9:
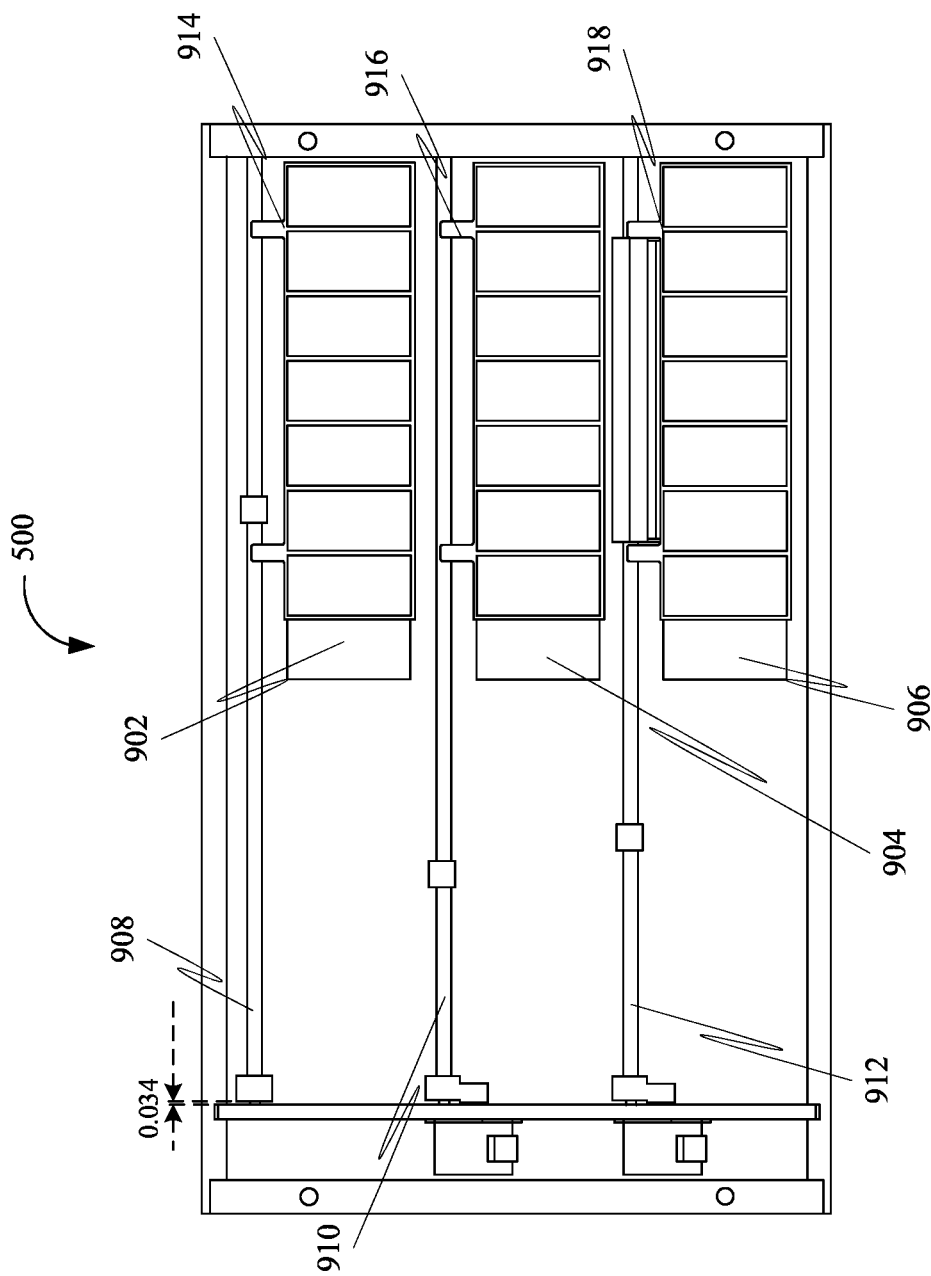
FIG. 9 is a front view of the base wall, in accordance with some embodiments.

FIG. 9 is a front view of the base wall 500 (similar to the base wall 212), in accordance with some embodiments. Further, at least one actuator 908-912 (similar to the at least one actuator 124) may be mechanically coupled with at least one of the bottomless tray 914-918 (similar to the at least one bottomless tray 206). Further, the at least one actuator 908-912 may facilitate linear motion of the at least one bottomless tray 914-918 with respect to the base wall 500 (similar to the base wall 212). Further, the linear motion of the at least one bottomless tray 914-918 may facilitate dispensing of the least one medication through at least one aperture 902-906 (similar to the at least one aperture 122).

Figure 10:
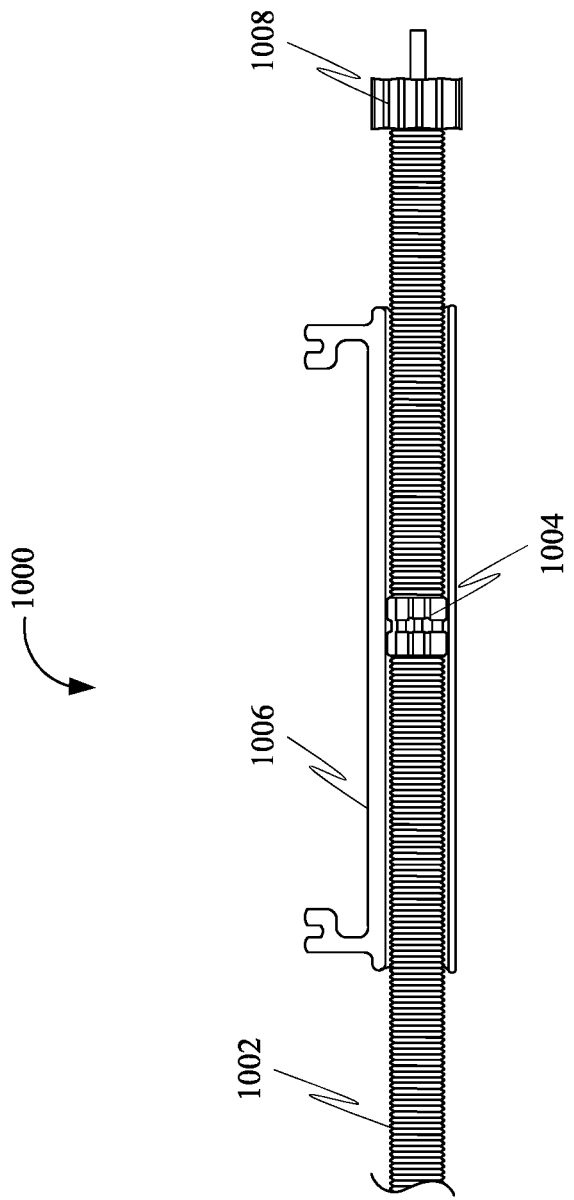
FIG. 10 is a front view of at least one actuator, in accordance with some exemplary embodiments.

FIG. 10 is a front view of at least one actuator 1000 (similar to the at least one actuator 224), in accordance with some exemplary embodiments. Further, the at least one actuator 1000 may include a rod 1002, a nut 1004, a mechanical coupler 1006, a gear assembly 1008, and a stepper motor (not shown). Further, the nut 1004 may include internal threading. Further, the nut 1004 may be configured to accommodate the rod 1002. Further, the rod 1002 may include external threading. Further, the nut 1004 may be threadedly coupled with the rod 1002 such that rotation of the rod 1002 may cause linear motion of the nut 1004. Further, the rod 1002 may be rotatably coupled to a rotor of the stepper motor through the gear assembly 1008. Further, the nut 1004 may be connected to the mechanical coupler 1006. Further, the mechanical coupler 1006 may include a diametrically cut hollow cylinder. Further, the inner diameter of the hollow cylinder may be equal to the outer diameter of the nut 1004. Further, the nut 1004 may be coaxially fixed to the concave surface of the mechanical coupler 1006. Further, the mechanical coupler 1006 may include at least one clamp. Further, the at least one clamp may be mechanically fixed on the convex surface of the mechanical coupler 1006. Further, the at least one clamp may facilitate the mechanical coupling of the mechanical coupler 1006 to the at least one bottomless tray 914-918 as shown in FIG. 9. Further, the rotary motion of the rotor of the stepper motor may be translated to the rotatory motion of the rod 1002. Further, the rotatory motion of the rod 1002 may be translated into the linear motion of the nut 1004. Further, the linear motion of the nut 1004 may be translated to the linear motion of the mechanical coupler 1006 and further, the linear motion of the at least one bottomless tray 914-918.

Figure 11:
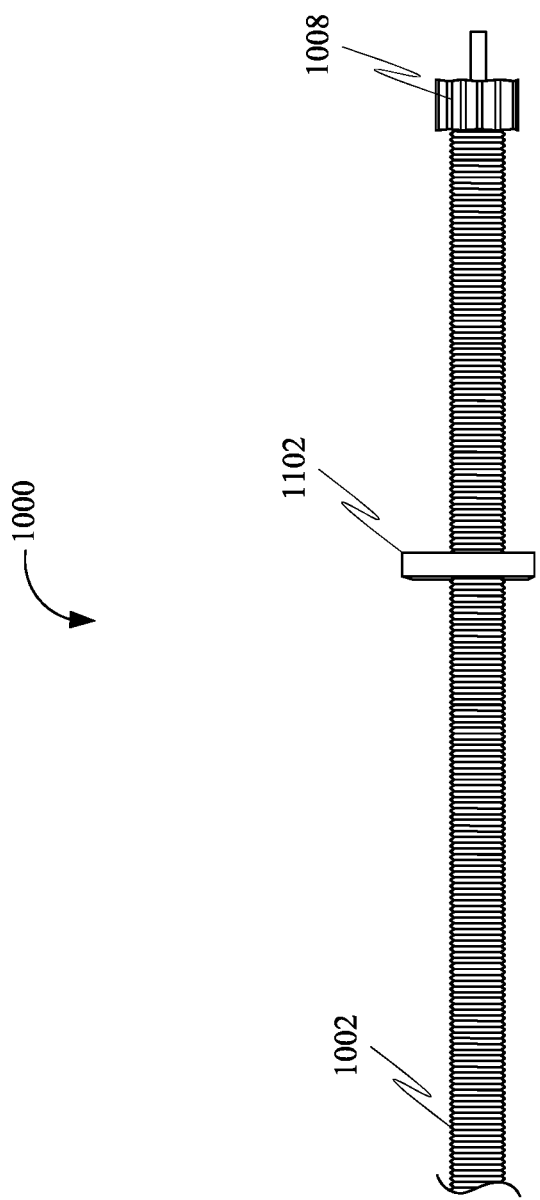
FIG. 11 is a front view the at least one actuator, in accordance with some exemplary embodiments.

FIG. 11 is a front view the at least one actuator 1000 (similar to the at least one actuator 224), in accordance with some exemplary embodiments. Further, the at least one actuator 1000 may include the rod 1002, the stepper motor, and the gear assembly 1006 as shown in the FIG. 10. Further, the at least one actuator 1000 may include a nut 1102. Further, the nut 1102 may include internal threading. Further, the nut 1102 may be configured to accommodate the rod 1002. Further, the rod 1002 may include external threading. Further, the nut 1102 may be threadedly coupled with the rod 1002 such that rotation of the rod 1002 may cause linear motion of the nut 1004. Further, the rod 1002 may be rotatably coupled to a rotor of the stepper motor through the gear assembly 1008. Further, the nut 1102 may be mechanically coupled with the at least one bottomless tray 914-918 as shown in FIG. 9. Further, the rotary motion of the rotor of the stepper motor may be translated to the rotatory motion of the rod 1002. Further, the rotatory motion of the rod 1002 may be translated into the linear motion of the nut 1004. Further, the linear motion of the nut 1004 may be translated to the linear motion of the at least one bottomless tray 914-918.

Figure 12:
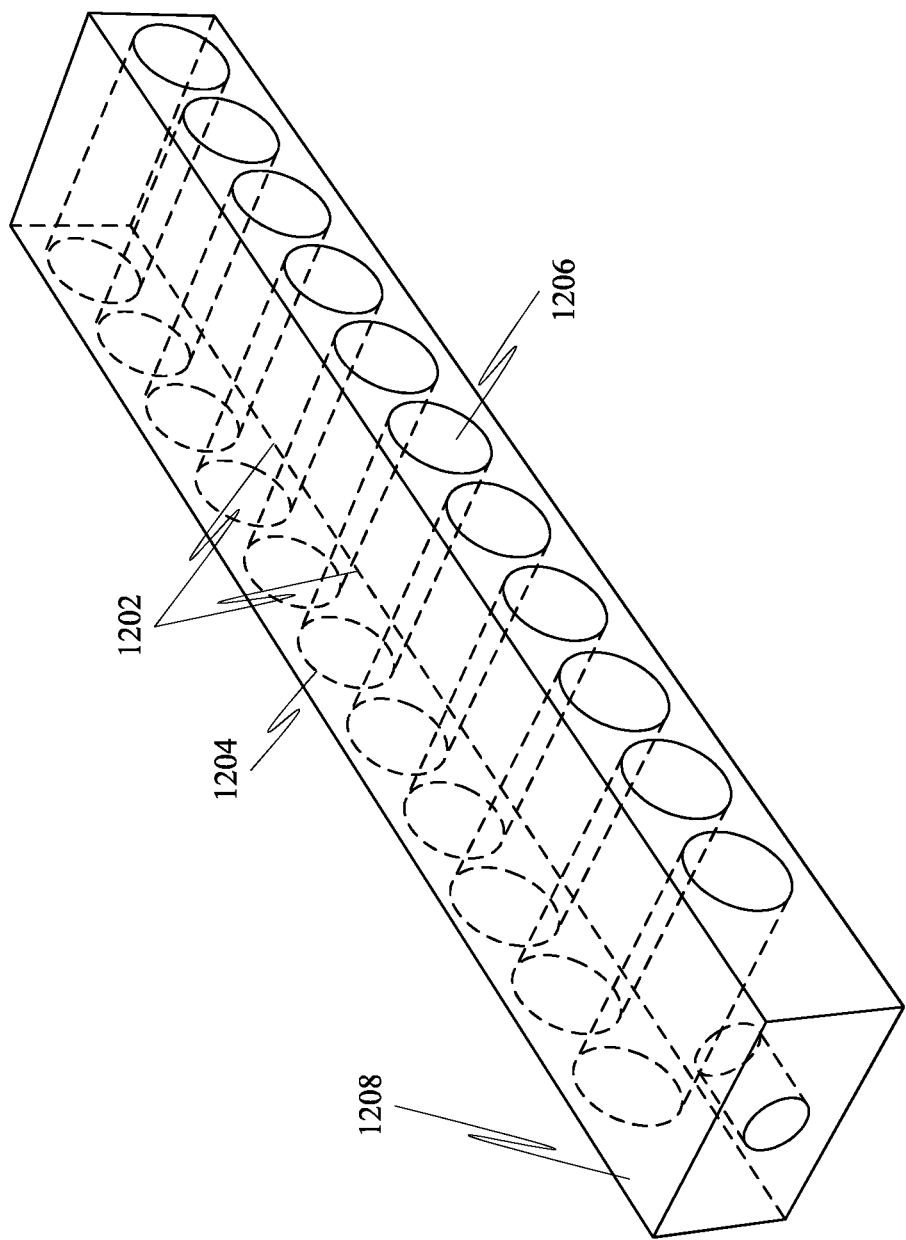
FIG. 12 is a front view of at least one bottomless tray, in accordance with some exemplary embodiments.

FIG. 12 is a front view of at least one bottomless tray 1208 (similar to the at least one bottomless tray 206), in accordance with some exemplary embodiments. Further, the at least one bottomless tray 1208 may include a plurality of compartments 1202 (similar to the plurality of compartments 214-218). Further, the plurality of compartments 1202 may include at least one compartment opening 1204-1206 (similar to the at least one compartment opening 220). Further, compartment openings of the at least one compartment opening 1204-1206 may be provided on two opposite side compartment wall of the at least one compartment wall.

Figure 13:
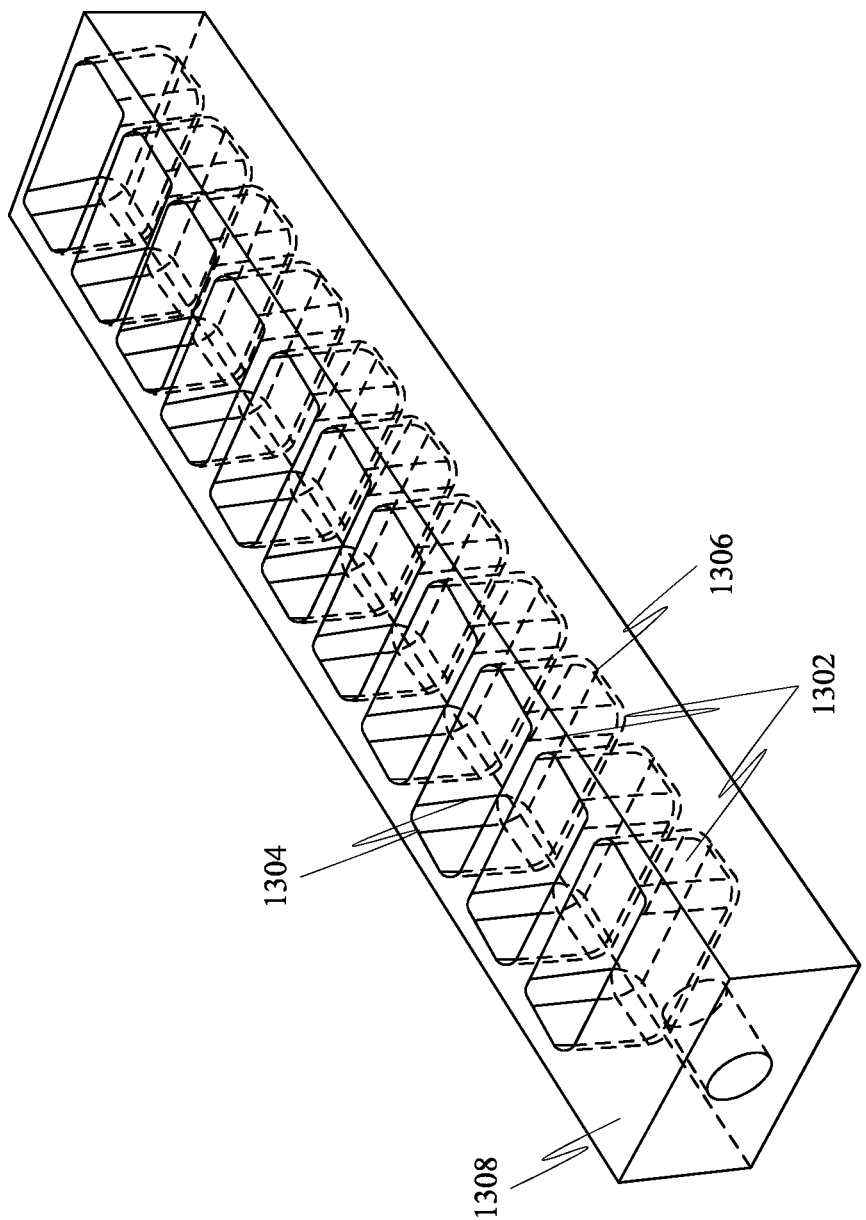
FIG. 13 is a front view of at least one bottomless tray, in accordance with some exemplary embodiments.

FIG. 13 is a front view of at least one bottomless tray 1308 (similar to the at least one bottomless tray 206), in accordance with some exemplary embodiments. Further, the at least one bottomless tray 1308 may include a plurality of compartments 1302 (similar to the plurality of compartments 214-218). Further, the plurality of compartments 1302 may include at least one compartment opening 1304-1306 (similar to the at least one compartment opening 220). Further, compartment openings of the at least one compartment opening 1304-1306 may be provided on the top and bottom compartment wall of the at least one compartment wall.

Figure 14:
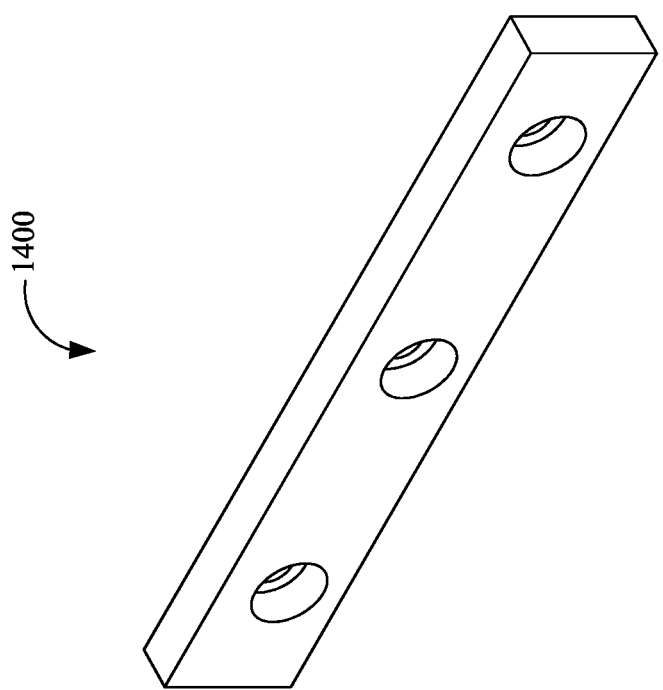
FIG. 14 is a front perspective view of a bearing wall, according to some embodiments.

FIG. 14 is a front perspective view of a bearing wall 1400, according to some embodiments. Further, the bearing wall may include at least one bearing. Further, the at least one bearing may be coaxially fixed to the rod 1002. Further, the bearing wall 1400 may provide mechanical support and facilitate the rotatory motion of the rod 1002 as shown in FIG. 10, of the at least one actuator 908-912, as shown in the FIG. 9.

Figure 15:
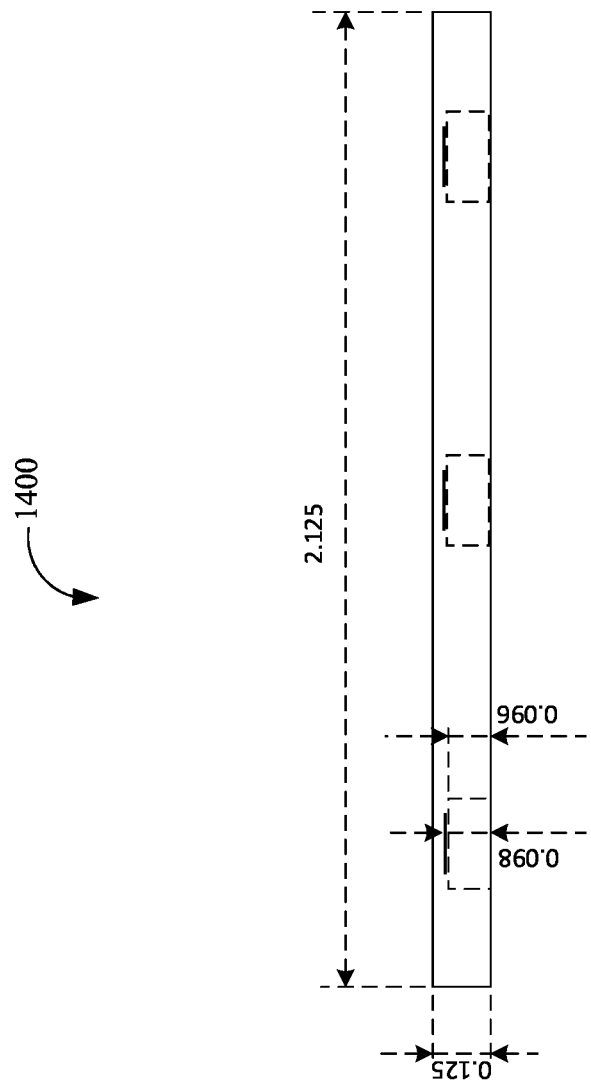
FIG. 15 is a side view of the bearing wall, according to some embodiments.

FIG. 15 is a side view of the bearing wall 1400, according to some embodiments. Further, the bearing wall 1400 may include a plurality of components. Further, an exemplary dimension of the plurality of components may be indicated. Further, the unit of the exemplary dimension may be "inch".

Figure 16:
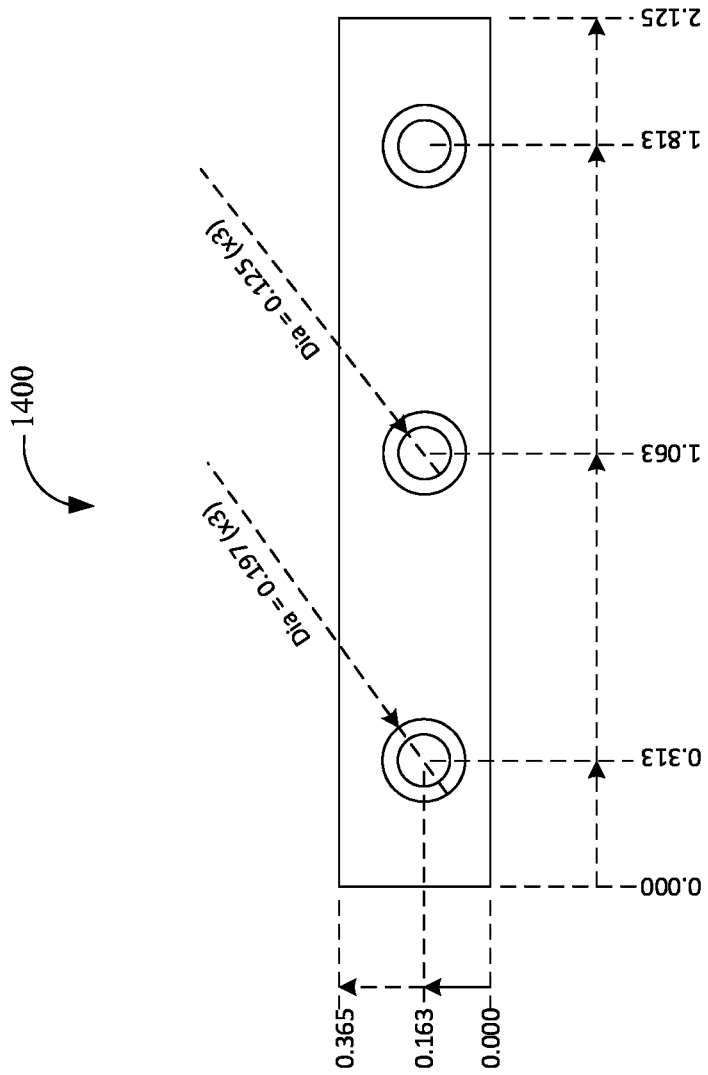
FIG. 16 is a front view of the bearing wall, according to some embodiments.

FIG. 16 is a front view of the bearing wall 1400, according to some embodiments. Further, the bearing wall 1400 may include a plurality of components. Further, an exemplary dimension of the plurality of components may be indicated. Further, the unit of the exemplary dimension may be "inch".

Figure 17:
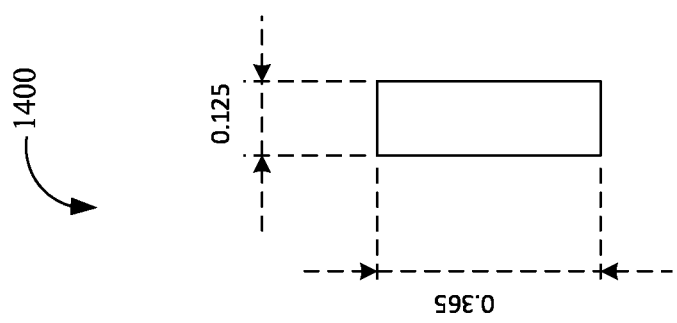
FIG. 17 is a top of the bearing wall, according to some embodiments.

FIG. 17 is a top of the bearing wall 1400, according to some embodiments. Further, the bearing wall 1400 may include a plurality of components. Further, an exemplary dimension of the plurality of components may be indicated. Further, the unit of the exemplary dimension may be "inch".

Figure 18:
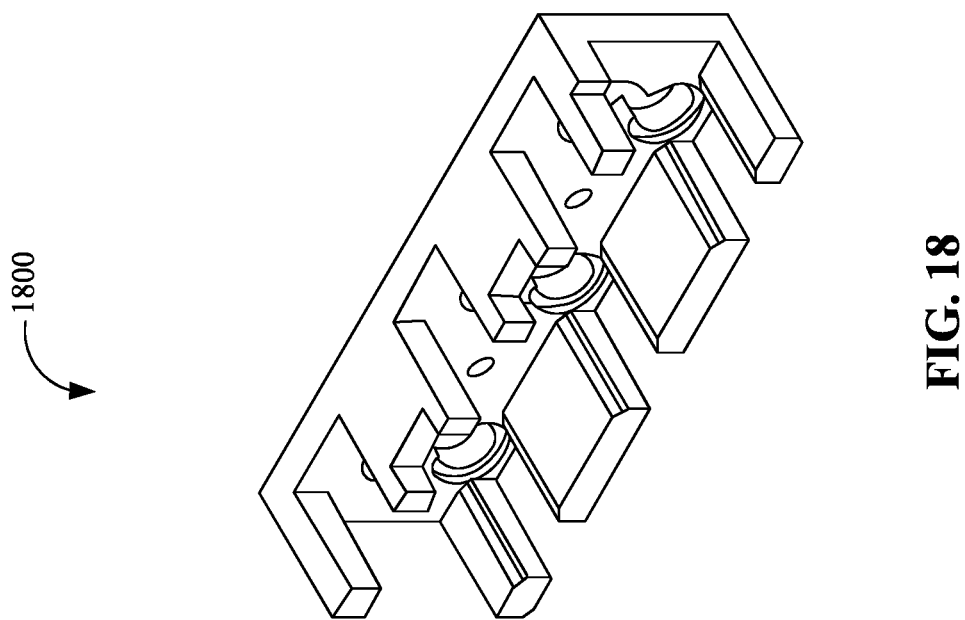
FIG. 18 is a front perspective view of a motor mount, according to some embodiments.

FIG. 18 is a front perspective view of a motor mount 1800, according to some embodiments. Further, the motor mount 1800 may provide an interior space to mount the stepper motor (not shown). Further, the motor mount 1800 may include at least one motor mount wall and at least one motor mount aperture on the at least one motor mount wall. Further, the motor mount 1800 may restrict any movement of the stepper motor while the stepper motor may be in an operation. Further, the motor mount 1800 may safeguard the stepper motor. Further, the motor mount 1800 may facilitate the uninterrupted operation of the stepper motor.

Figure 19:
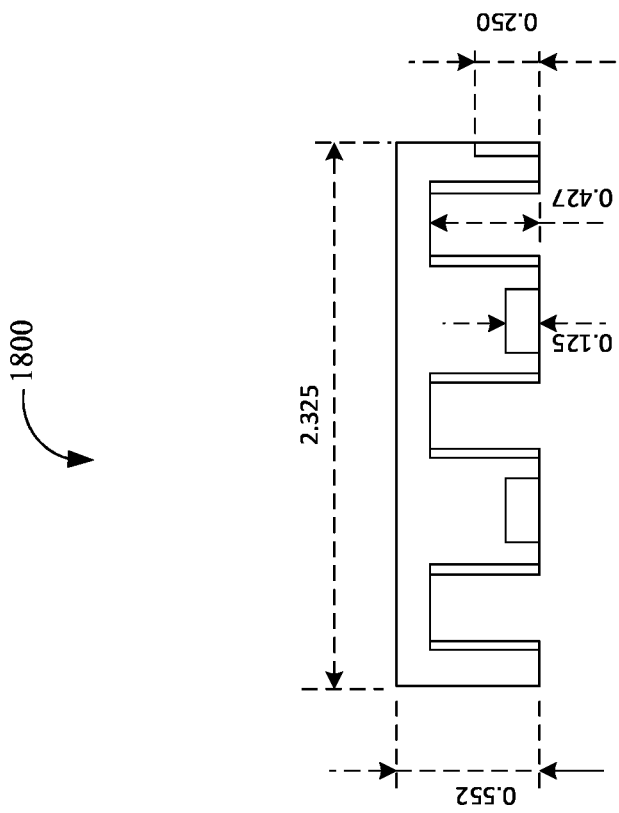
FIG. 19 is a side view of the motor mount, according to some embodiments.

FIG. 19 is a side view of the motor mount 1800, according to some embodiments. Further, the motor mount 1800 may include a plurality of components. Further, an exemplary dimension of the plurality of components may be indicated. Further, the unit of the exemplary dimension may be "inch".

Figure 20:
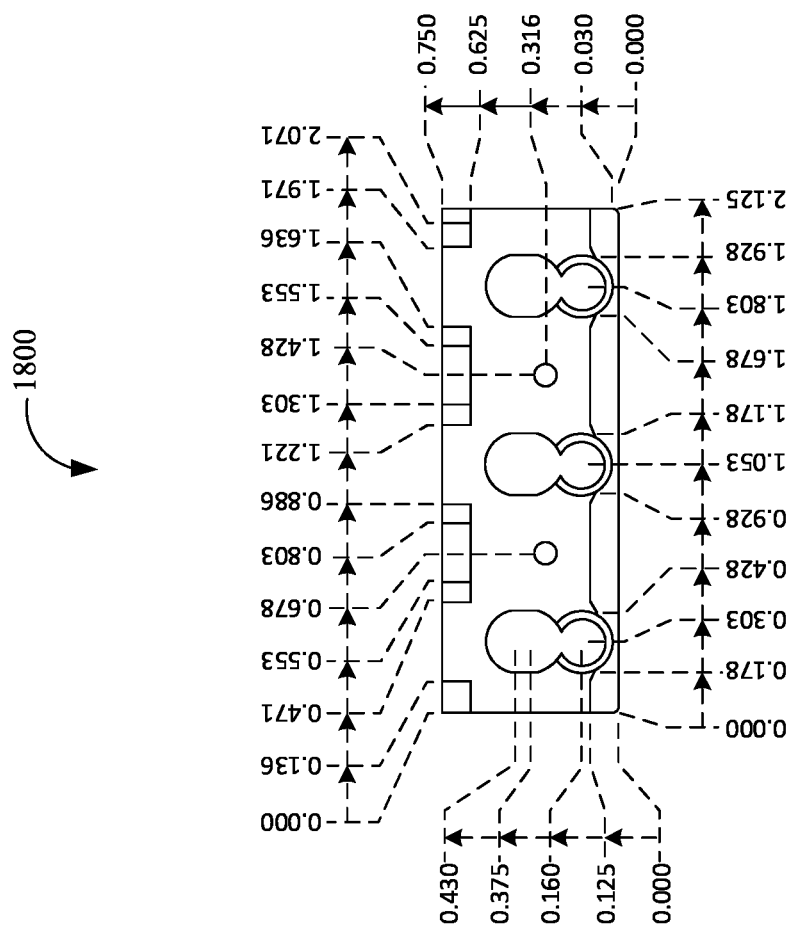
FIG. 20 is a front view of the motor mount, according to some embodiments.

FIG. 20 is a front view of the motor mount 1800, according to some embodiments. Further, the bearing wall 1400 may include a plurality of components. Further, an exemplary dimension of the plurality of components may be indicated. Further, the unit of the exemplary dimension may be "inch".

Figure 21:
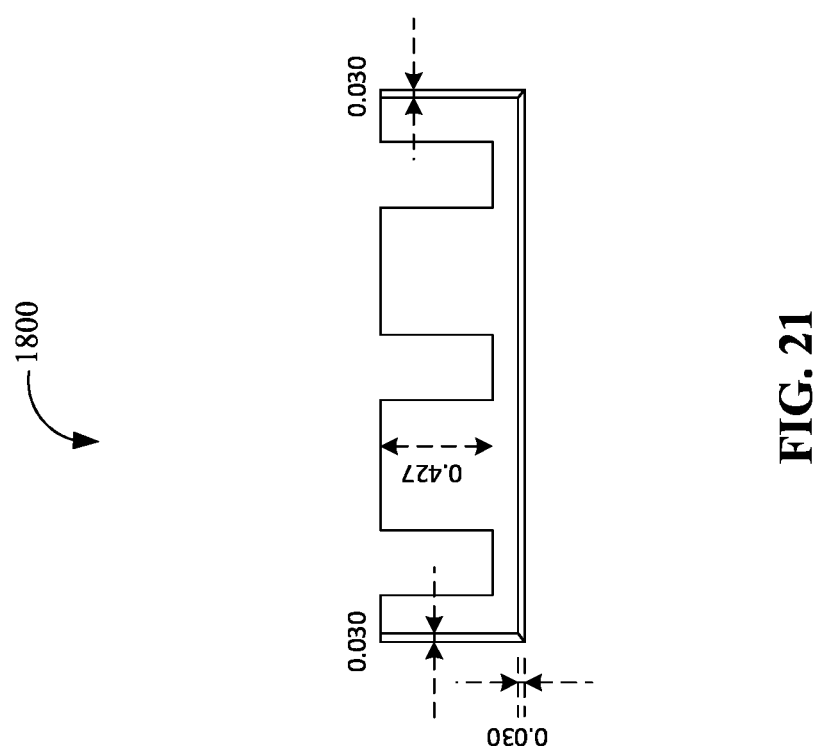
FIG. 21 is a side perspective view of the motor mount, according to some embodiments.

FIG. 21 is a side perspective view of the motor mount 1800, according to some embodiments. Further, the motor mount 1800 may include a plurality of components. Further, an exemplary dimension of the plurality of components may be indicated. Further, the unit of the exemplary dimension may be "inch".

Figure 22:
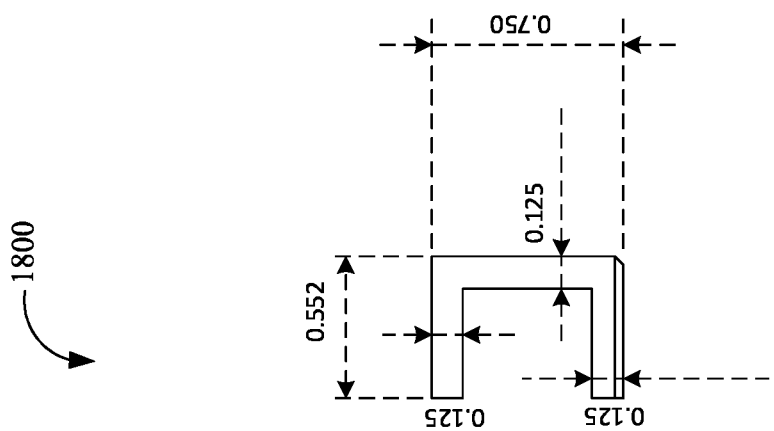
FIG. 22 is a top view of the motor mount, according to some embodiments.

FIG. 22 is a top view of the motor mount 1800, according to some embodiments. Further, the motor mount 1800 may include a plurality of components. Further, an exemplary dimension of the plurality of components may be indicated. Further, the unit of the exemplary dimension may be "inch".

Figure 23:
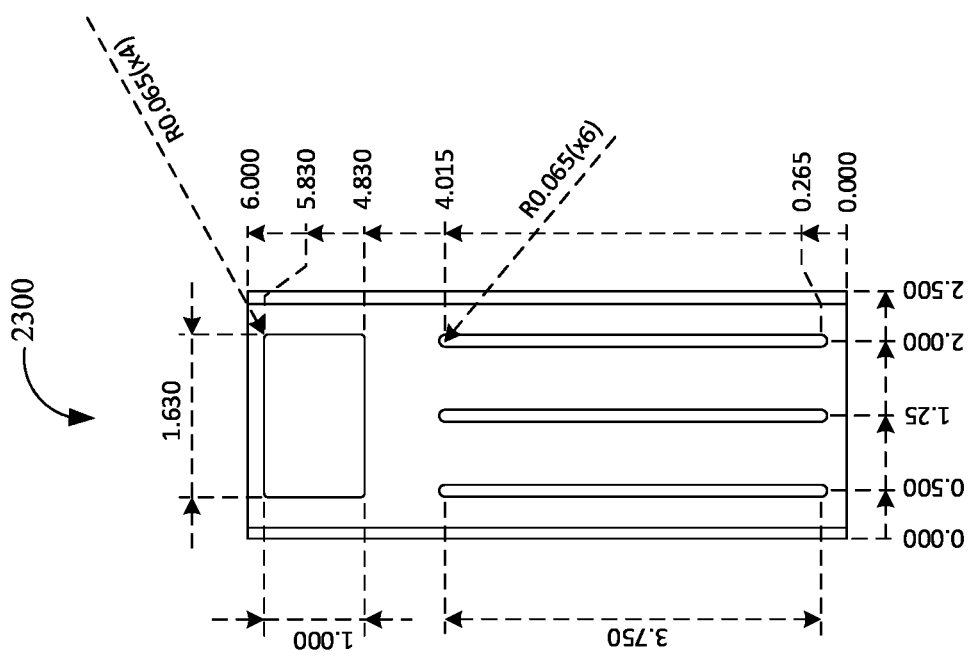
FIG. 23 is a front view of a housing of the programmable medication dispenser, according to some exemplary embodiments.

FIG. 23 is a front view of a housing 2300 (similar to the housing 202) of the programmable medication dispenser 200, according to some exemplary embodiments. Further, the housing 2300 may include a plurality of components. Further, an exemplary dimension of the plurality of components may be indicated. Further, the unit of the exemplary dimension may be "inch".

Figure 24:
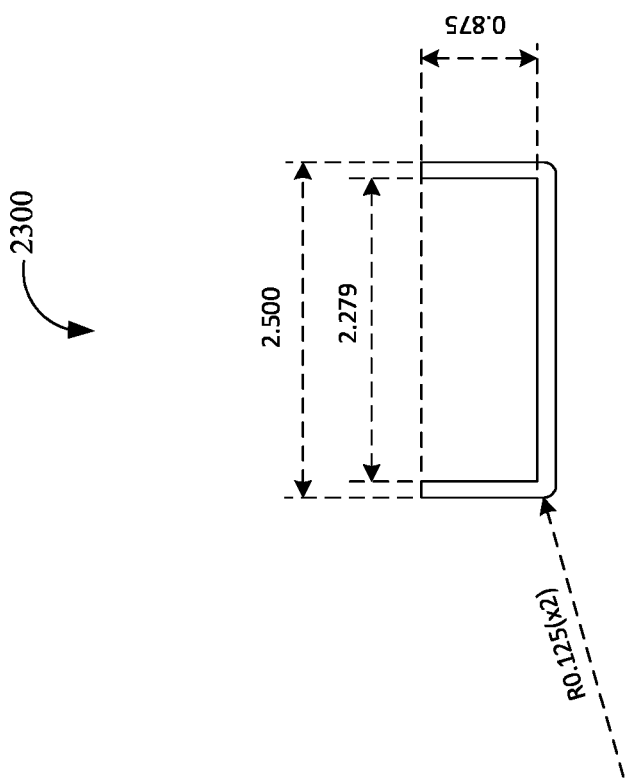
FIG. 24 is a top view of the housing of the programmable medication dispenser, according to some exemplary embodiments.

FIG. 24 is a top view of the housing 2300 of the programmable medication dispenser 200, according to some exemplary embodiments. Further, the housing 2300 may include a plurality of components. Further, an exemplary dimension of the plurality of components may be indicated. Further, the unit of the exemplary dimension may be "inch".

Figure 25:
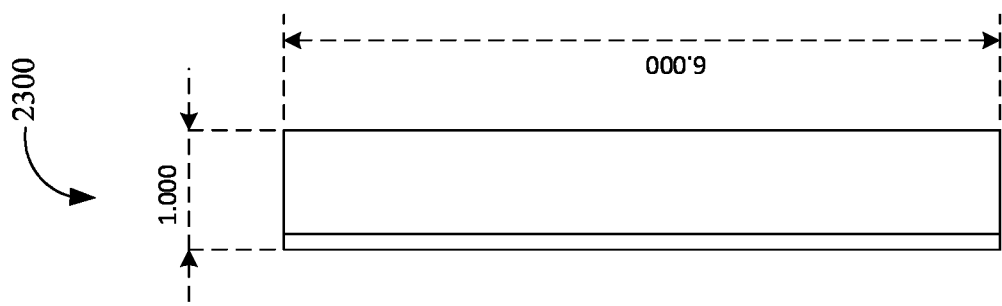
FIG. 25 is a side view of the housing of the programmable medication dispenser, according to some exemplary embodiments.

FIG. 25 is a side view of the housing 2300 of the programmable medication dispenser 200, according to some exemplary embodiments. Further, the housing 2300 may include a plurality of components. Further, an exemplary dimension of the plurality of components may be indicated. Further, the unit of the exemplary dimension may be "inch".

Figure 26:
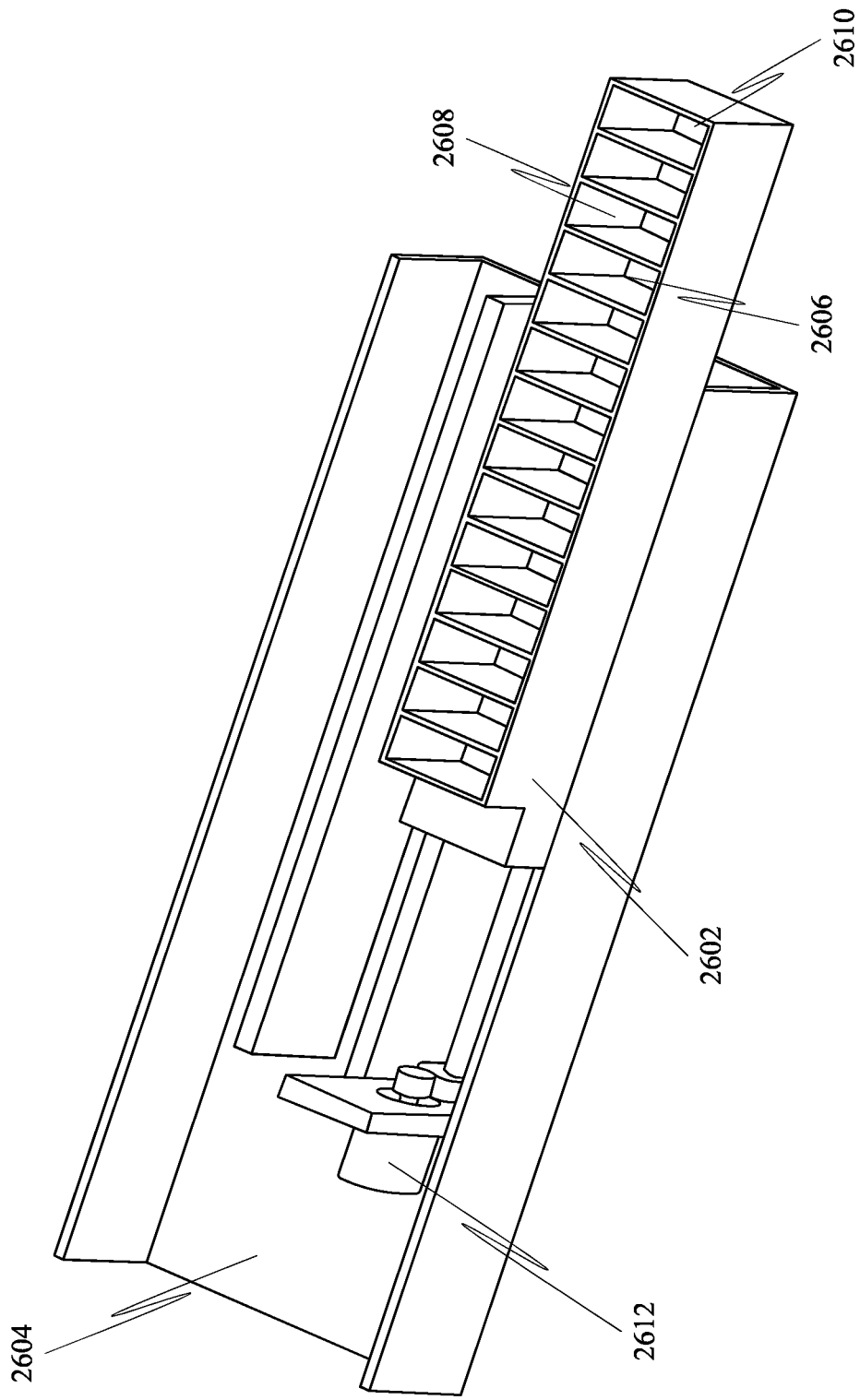
FIG. 26 is a front perspective view of a base wall of the programmable medication dispenser, according to some exemplary embodiments.

FIG. 26 is a front perspective view of a base wall 2604 (similar to the base wall 212) of the programmable medication dispenser, according to some exemplary embodiments. Further, the base wall 2604 may include at least one bottomless tray 2602 (similar to the at least one bottomless tray 206). Further, the at least one bottomless tray 2602 may include a plurality of compartments 2606-2608 (similar to the plurality of compartments 214-218). Further, the base wall 2604 may include at least one actuator 2612 (similar to the at least one actuator 224). Further, the at least one actuator 2612 may be mechanically coupled with the at least one bottomless tray 2602. Further, the at least one actuator 2612 may provide linear motion to the at least one bottomless tray 2602 with respect to the base wall 2604.

Figure 27:
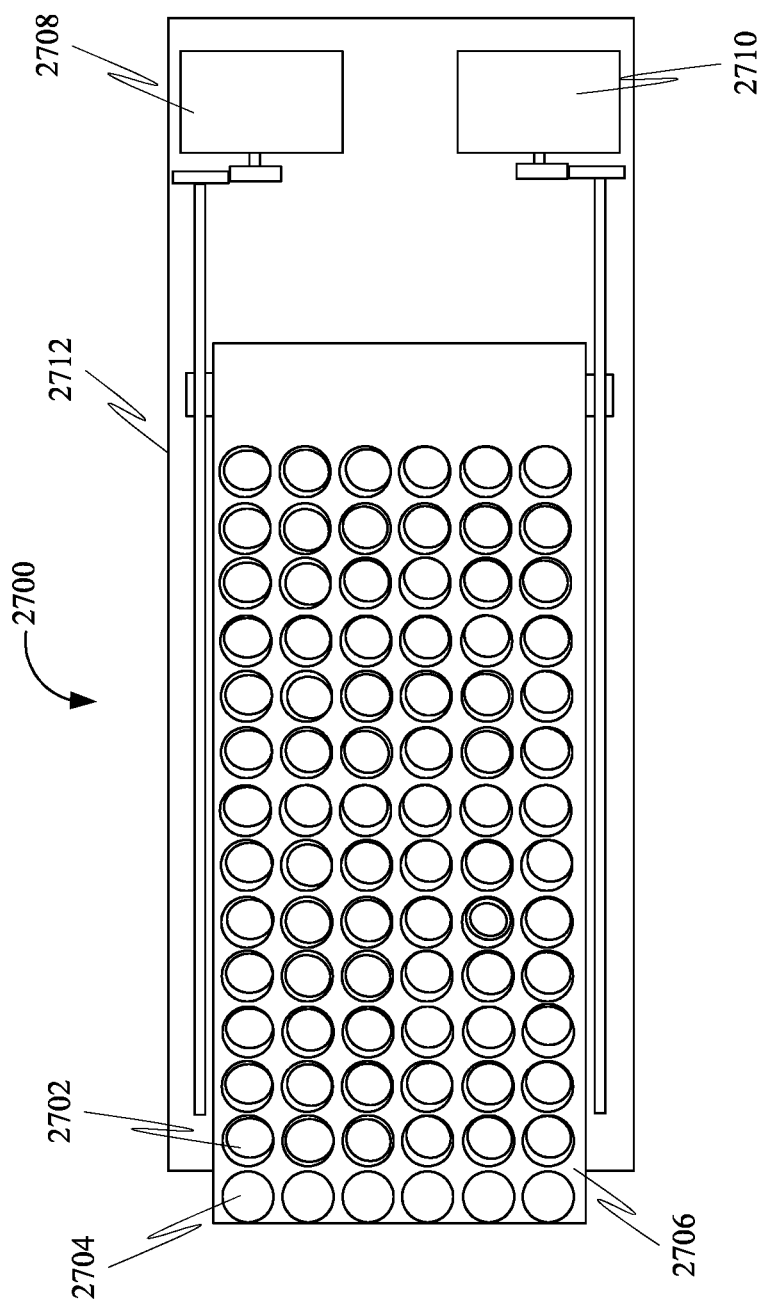
FIG. 27 is a top cross-sectional view of the programmable medication dispenser, in accordance with some exemplary embodiments.

FIG. 27 is a top cross-sectional view of the programmable medication dispenser 2700, in accordance with some exemplary embodiments. Further, the programmable medication dispenser may include a housing 2712 (similar to the housing 202). Further, the housing 2712 may include at least one bottomless tray 2706 (similar to the at least one bottomless tray 206). Further, the bottomless tray 2706 may include a plurality of compartments 2702-2704 (similar to the plurality of compartments 214-218). Further, the plurality of the compartments may accommodate at least one medication. Further, the housing 2712 may include at least one actuator 2708-2710 (similar to at least one actuator 224). Further, the at least one actuator 2708-2710 may be mechanically coupled with the at least one bottomless tray 2706. Further, the at least one actuator 2708-2710 may provide linear motion to the at least one bottomless tray 2706 with respect to the housing 2712. Further, the linear motion may displace the bottomless tray 2706 to a plurality of positions exterior and/or interior to the housing 2712. Further, at least one compartment of the plurality of the compartments 2702-2704 may be externally accessible when the at least one bottomless tray 2706 may be displaced exterior to the housing 2712. Further, the at least one compartment of the plurality of compartments 2702-2704 may not be externally accessible when at least one bottomless tray 2706 may be displaced interior to the housing 2712.

Figure 28:
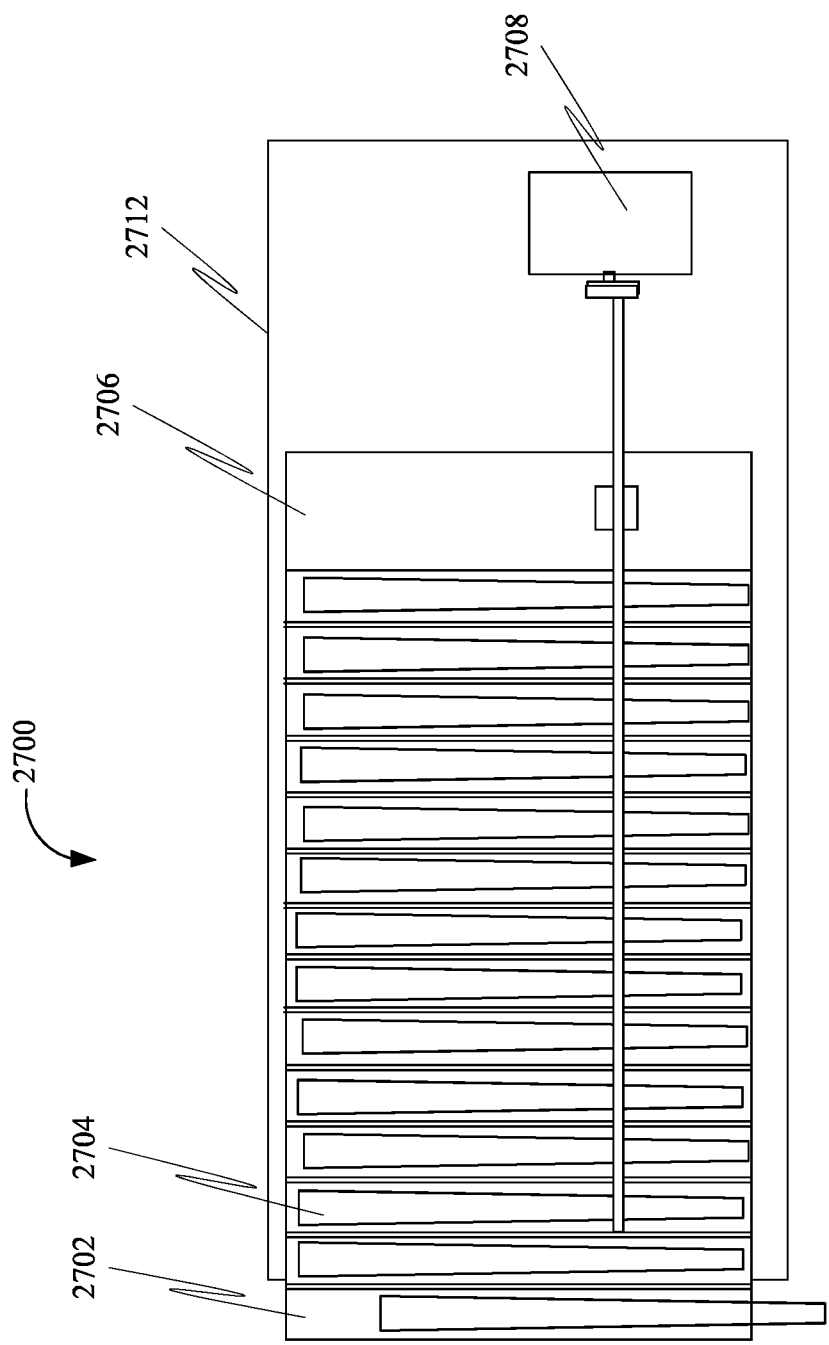
FIG. 28 is a side cross-sectional view of the programmable medication dispenser, in accordance with some exemplary embodiments.

FIG. 28 is a side cross-sectional view of the programmable medication dispenser 2700, in accordance with some exemplary embodiments.

Figure 29:
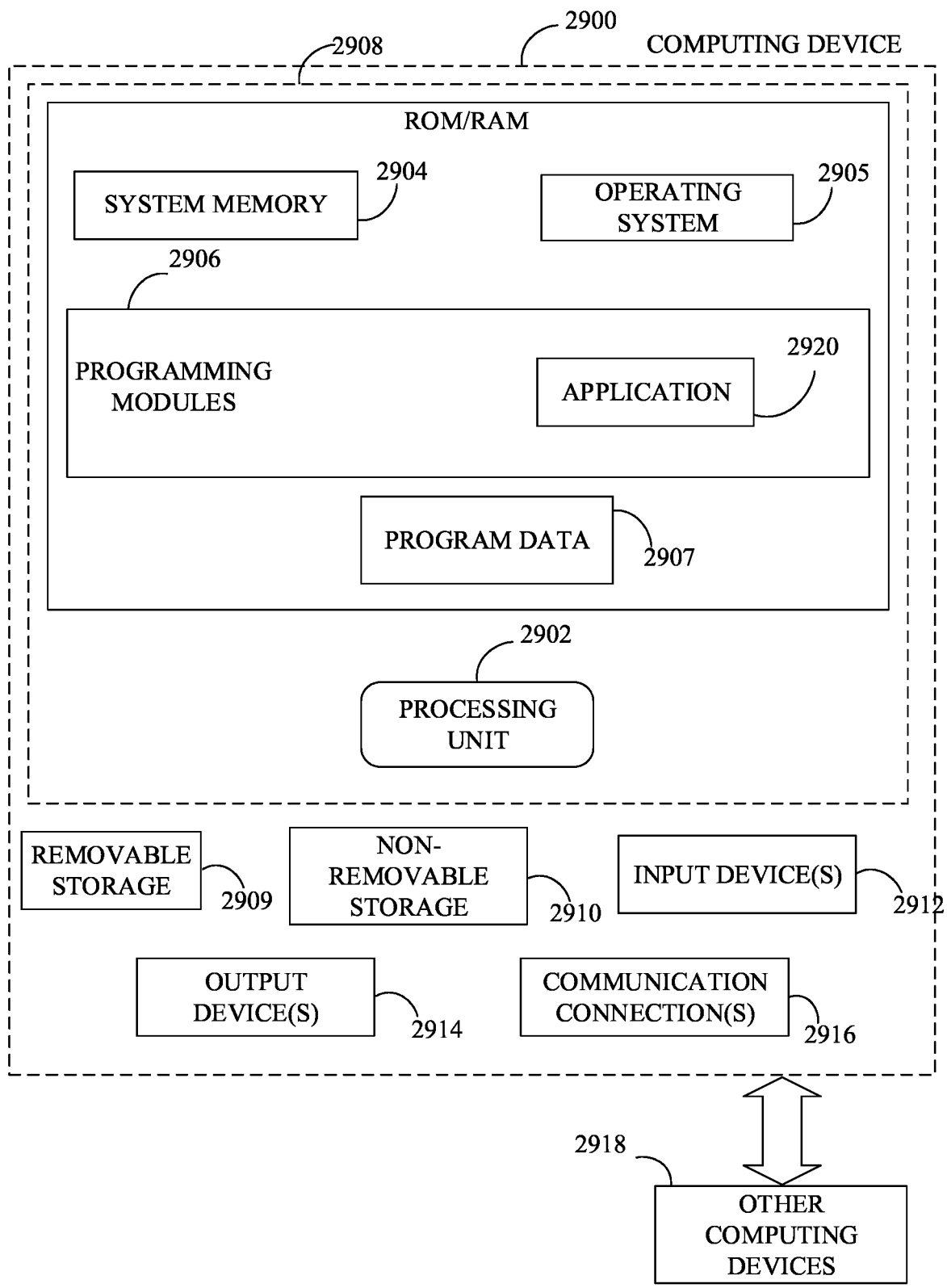
FIG. 29 is a block diagram of a computing device for implementing the methods disclosed herein, in accordance with some embodiments.

With reference to FIG. 29, a system consistent with an embodiment of the disclosure may include a computing device or cloud service, such as computing device 2900. In a basic configuration, computing device 2900 may include at least one processing unit 2902 and a system memory 2904. Depending on the configuration and type of computing device, system memory 2904 may comprise, but is not limited to, volatile (e.g. random-access memory (RAM)), non-volatile (e.g. read-only memory (ROM)), flash memory, or any combination. System memory 2904 may include operating system 2905, one or more programming modules 2906, and may include a program data 2907. Operating system 2905, for example, may be suitable for controlling computing device 2900's operation. In one embodiment, programming modules 2906 may include image-processing module, machine learning module. Furthermore, embodiments of the disclosure may be practiced in conjunction with a graphics library, other operating systems, or any other application program and is not limited to any particular application or system. This basic configuration is illustrated in FIG. 29 by those components within a dashed line 2908.

Computing device 2900 may have additional features or functionality. For example, computing device 2900 may also include additional data storage devices (removable and/or non-removable) such as, for example, magnetic disks, optical disks, or tape. Such additional storage is illustrated in FIG. 29 by a removable storage 2909 and a non-removable storage 2910. Computer storage media may include volatile and non-volatile, removable and non-removable media implemented in any method or technology for storage of information, such as computer-readable instructions, data structures, program modules, or other data. System memory 2904, removable storage 2909, and non-removable storage 2910 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 2900. Any such computer storage media may be part of device 2900. Computing device 2900 may also have input device(s) 2912 such as a keyboard, a mouse, a pen, a sound input device, a touch input device, a location sensor, a camera, a biometric sensor, etc. Output device(s) 2914 such as a display, speakers, a printer, etc. may also be included. The aforementioned devices are examples and others may be used.

Computing device 2900 may also contain a communication connection 2916 that may allow device 2900 to communicate with other computing devices 2918, such as over a network in a distributed computing environment, for example, an intranet or the Internet. Communication connection 2916 is one example of communication media. Communication media may typically be embodied by computer-readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer-readable media as used herein may include both storage media and communication media.

As stated above, a number of program modules and data files may be stored in system memory 2904, including operating system 2905. While executing on processing unit 2902, programming modules 2906 (e.g., application 2920 such as a media player) may perform processes including, for example, one or more stages of methods, algorithms, systems, applications, servers, databases as described above. The aforementioned process is an example, and processing unit 2902 may perform other processes. Other programming modules that may be used in accordance with embodiments of the present disclosure may include machine learning applications.

Generally, consistent with embodiments of the disclosure, program modules may include routines, programs, components, data structures, and other types of structures that may perform particular tasks or that may implement particular abstract data types. Moreover, embodiments of the disclosure may be practiced with other computer system configurations, including hand-held devices, general-purpose graphics processor-based systems, multiprocessor systems, microprocessor-based or programmable consumer electronics, application-specific integrated circuit-based electronics, minicomputers, mainframe computers, and the like. Embodiments of the disclosure may also be practiced in distributed computing environments where tasks are performed by remote processing devices that are linked through a communications network. In a distributed computing environment, program modules may be located in both local and remote memory storage devices.

Furthermore, embodiments of the disclosure may be practiced in an electrical circuit comprising discrete electronic elements, packaged or integrated electronic chips containing logic gates, a circuit utilizing a microprocessor, or on a single chip containing electronic elements or microprocessors. Embodiments of the disclosure may also be practiced using other technologies capable of performing logical operations such as, for example, AND, OR, and NOT, including but not limited to mechanical, optical, fluidic, and quantum technologies. In addition, embodiments of the disclosure may be practiced within a general-purpose computer or in any other circuits or systems.

Embodiments of the disclosure, for example, may be implemented as a computer process (method), a computing system, or as an article of manufacture, such as a computer program product or computer-readable media. The computer program product may be a computer storage media readable by a computer system and encoding a computer program of instructions for executing a computer process. The computer program product may also be a propagated signal on a carrier readable by a computing system and encoding a computer program of instructions for executing a computer process. Accordingly, the present disclosure may be embodied in hardware and/or in software (including firmware, resident software, micro-code, etc.). In other words, embodiments of the present disclosure may take the form of a computer program product on a computer-usable or computer-readable storage medium having computer-usable or computer-readable program code embodied in the medium for use by or in connection with an instruction execution system. A computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific computer-readable medium examples (a non-exhaustive list), the computer-readable medium may include the following: an electrical connection having one or more wires, a portable computer diskette, a random-access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory.

Embodiments of the present disclosure, for example, are described above with reference to block diagrams and/or operational illustrations of methods, systems, and computer program products according to embodiments of the disclosure. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the disclosure have been described, other embodiments may exist. Furthermore, although embodiments of the present disclosure have been described as being associated with data stored in memory and other storage mediums, data can also be stored on or read from other types of computer-readable media, such as secondary storage devices, like hard disks, solid-state storage (e.g., USB drive), or a CD-ROM, a carrier wave from the Internet, or other forms of RAM or ROM. Further, the disclosed methods' stages may be modified in any manner, including by reordering stages and/or inserting or deleting stages, without departing from the disclosure.

Figure 30:
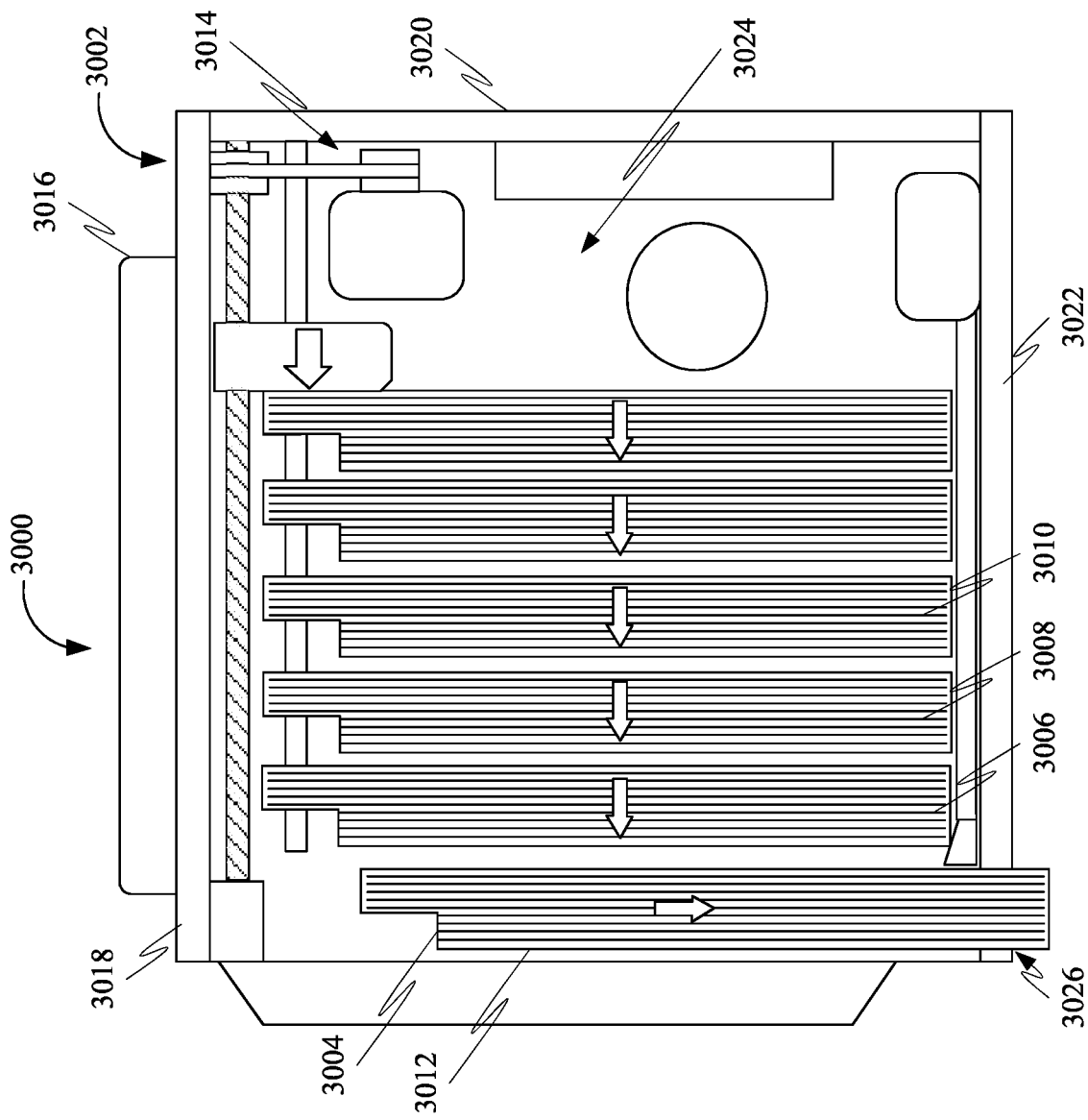
FIG. 30 is a side cross-sectional view of an apparatus for facilitating refilling of medication into a programmable medication dispenser, in accordance with some embodiments.

FIG. 30 is a side cross-sectional view of an apparatus 3000 for facilitating refilling of medication into a programmable medication dispenser, in accordance with some embodiments. Further, the apparatus 3000 may include an apparatus body 3002, at least one bottomless tray 3004-3010, at least one cover 3012, at least one refilling actuator 3014, and at least one power source 3016.

Further, the apparatus body 3002 may include at least one body wall 3018-3022 and at least one body interior space 3024 formed by the at least one body wall 3018-3022. Further, the at least one body wall 3018-3022 may include at least one body opening 3026 leading into the at least one body interior space 3024.

Further, the at least one bottomless tray 3004-3010 may be configured to be movably disposed within the at least one body interior space 3024. Further, the at least one bottomless tray 3004-3010 may include a plurality of compartments. Further, each compartment of the plurality of compartments may include at least one compartment opening and at least one compartment wall forming a corresponding compartment. Further, the plurality of compartments may include at least one medication.

Further, the at least one cover 3012 may be removably attached to at least one side of the at least one bottomless tray 3004-3010 for securing the at least one medication in the plurality of compartments. Further, the at least one cover 3012 may include a cellophane cover.

Further, the at least one refilling actuator 3014 may be coupled with the at least one bottomless tray 3004-3010. Further, the at least one refilling actuator 3014 may be configured for displacing the at least one bottomless tray 3004-3010 from at least one storage position to a dispensing position within the at least one body interior space 3024. Further, the at least one bottomless tray 3004-3010 may be dispensable through the at least one body opening 3026 in the dispensing position. Further, the at least one bottomless tray 3004-3010 may not be dispensable through the at least one body opening 3026 in the at least one storage position. Further, the programmable medication dispenser receives the at least one bottomless tray 3004-3010 through the at least one body opening 3026 based on dispensing of the at least one bottomless tray 3004-3010 through the at least one body opening 3026.

Further, at least one power source 3016 may be coupled with the at least one refilling actuator 3014. Further, the at least one power source 3016 may be configured for powering the at least one refilling actuator 3014. Further, at least one power source 3016 may include at least one battery.

Figure 31:
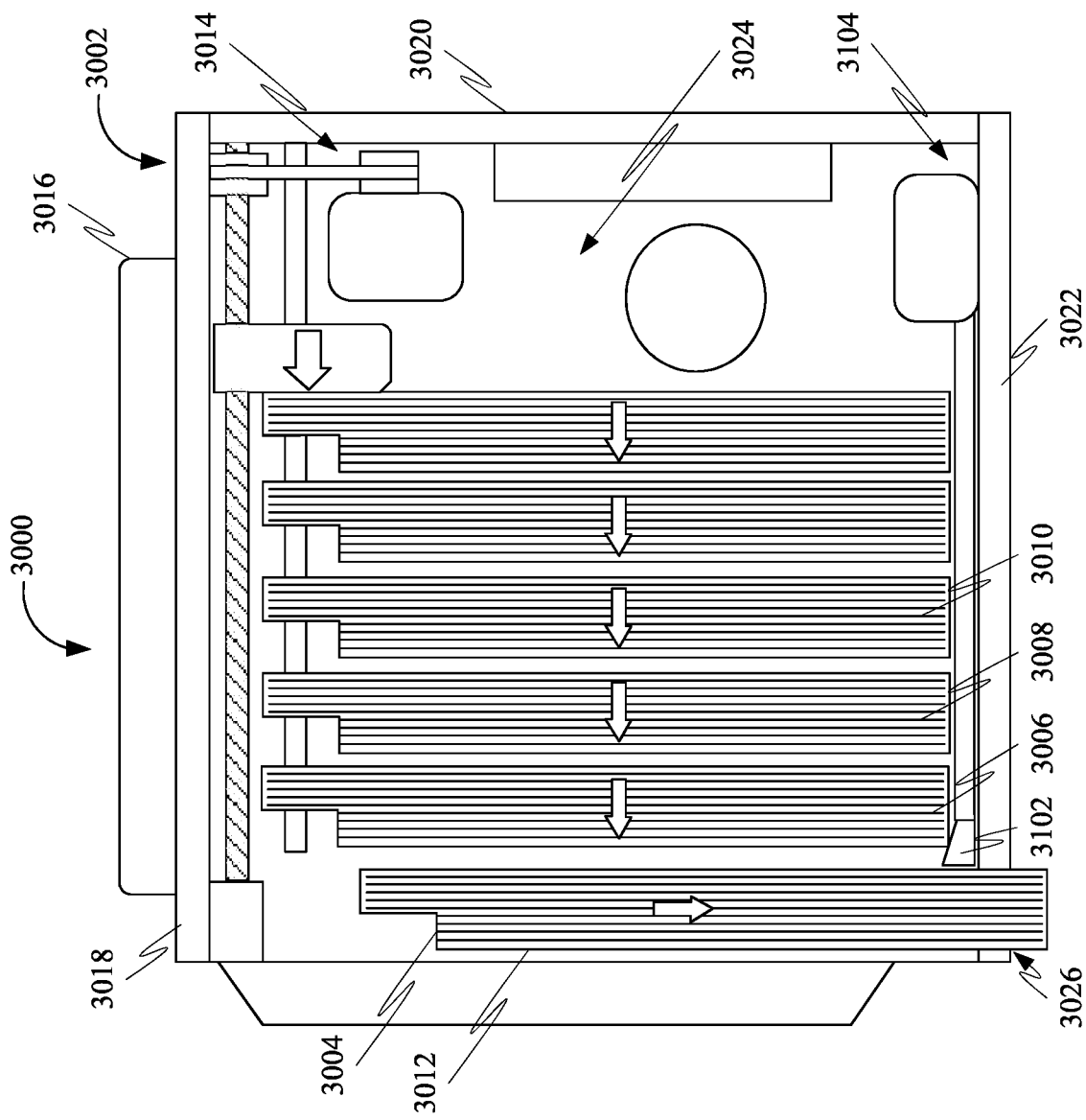
FIG. 31 is a side cross-sectional view of the apparatus, in accordance with some embodiments.

In further embodiments, the apparatus 3000 may include at least one lid 3102, as shown in FIG. 31, coupled with the at least one body opening 3026. Further, the at least one lid 3102 may include a wedge. Further, the at least one lid 3102 may be configured for transitioning between an open state and a closed state. Further, the at least one lid 3102 covers the at least body opening 3026 for preventing the dispensing of the at least one bottomless tray 3004-3010 through the at least one body opening 3026 in the closed state. Further, the at least one lid 3102 does not cover the at least one body opening 3026 for allowing the dispensing of the at least one bottomless tray 3004-3010 through the at least one body opening 3026 in the open state.

In further embodiments, the apparatus 3000 may include at least one lid actuator 3104, as shown in FIG. 31, coupled with the at least one lid 3102. Further, the at least one lid actuator 3104 may be configured for displacing the at least one lid 3102 between an open position and a closed position for the transitioning of the at least one lid 3102. Further, the open position corresponds to the open state and the closed position corresponds to the closed state. Further, the at least one power source 3016 may be coupled with the at least one lid actuator 3104. Further, the at least one power source 3016 may be configured for powering the at least one lid actuator 3104.

Figure 32:
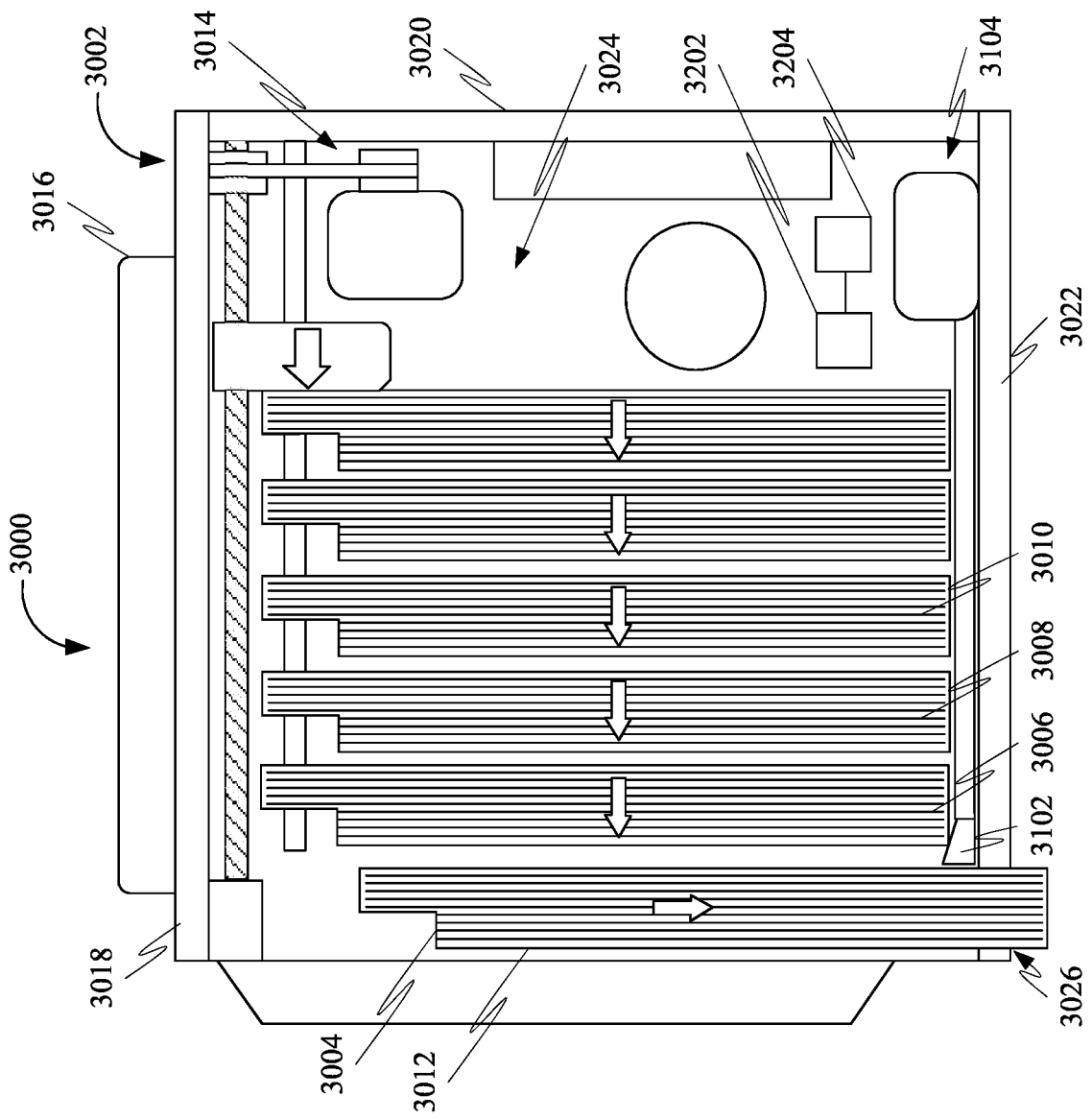
FIG. 32 is a side cross-sectional view of the apparatus, in accordance with some embodiments.

In further embodiments, the apparatus 3000 may include at least one first sensor 3202 and a processing device 3204, as shown in FIG. 32. Further, the at least one first sensor 3202 may be disposed in the at least one body interior space 3024. Further, the at least one first sensor 3202 may be configured for generating at least one first sensor data based on a position of the at least one bottomless tray 3004-3010 in relation to the at least one body opening 3026. Further, the processing device 3204 may be disposed on the apparatus body 3002. Further, the processing device 3204 may be communicatively coupled with the at least one first sensor 3202. Further, the processing device 3204 may be configured for analyzing the at least one first sensor data. Further, the processing device 3204 may be configured for determining a dispensing state of the at least bottomless tray based on the analyzing. Further, the processing device 3204 may be configured for generating at least one lid control command based on the determining. Further, the processing device 3204 may be communicatively coupled with the at least one lid actuator 3104. Further, the displacing of the at least one lid 3102 between the open position and the closed position may be based on the at least one lid control command.

Figure 33:
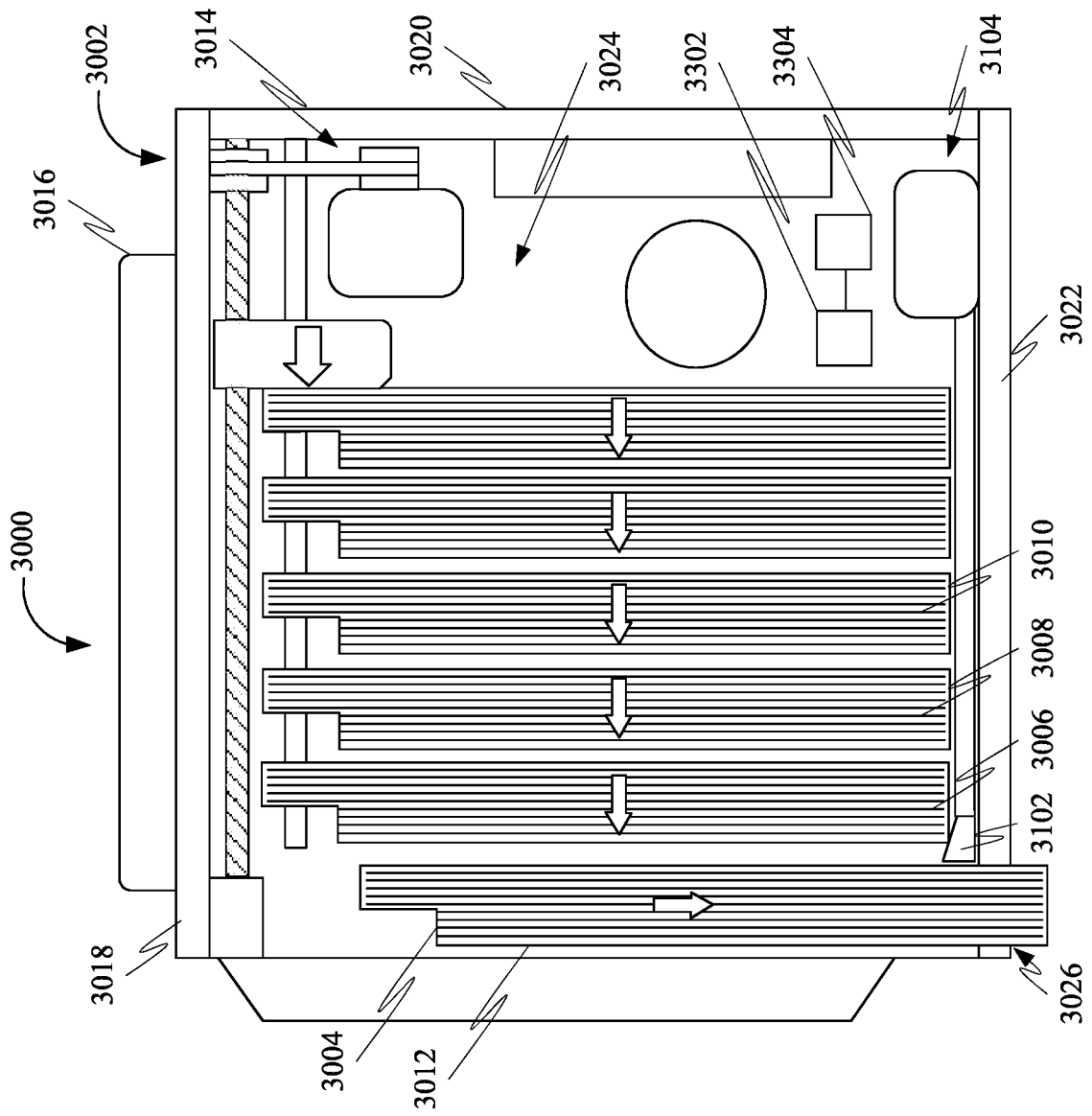
FIG. 33 is a side cross-sectional view of the apparatus, in accordance with some embodiments.

In further embodiments, the apparatus 3000 may include at least one sensor 3302 and a processing device 3304, as shown in FIG. 33. Further, the at least one sensor 3302 may be disposed in the at least one body interior space 3024. Further, the at least one sensor 3302 may be configured for generating at least one sensor data based on at least one of a relative position and a relative orientation of the at least one bottomless tray 3004-3010 in relation to the at least one body opening 3026. Further, the processing device 3304 may include disposed on the apparatus body 3002. Further, the processing device 3304 may be communicatively coupled with the at least one sensor 3302. Further, the processing device 3304 may be configured for analyzing the at least one sensor data. Further, the processing device 3304 may be configured for determining at least one displacement condition for the displacing of the at least one bottomless tray 3004-3010 based on the analyzing. Further, the processing device 3304 may be configured for generating at least one displacement command for the displacing of the at least one bottomless tray 3004-3010 based on the determining. Further, the processing device 3304 may be communicatively coupled with the at least one refilling actuator 3014. Further, the displacing of the at least one bottomless tray 3004-3010 may be based on the at least one displacement command.

Figure 34:
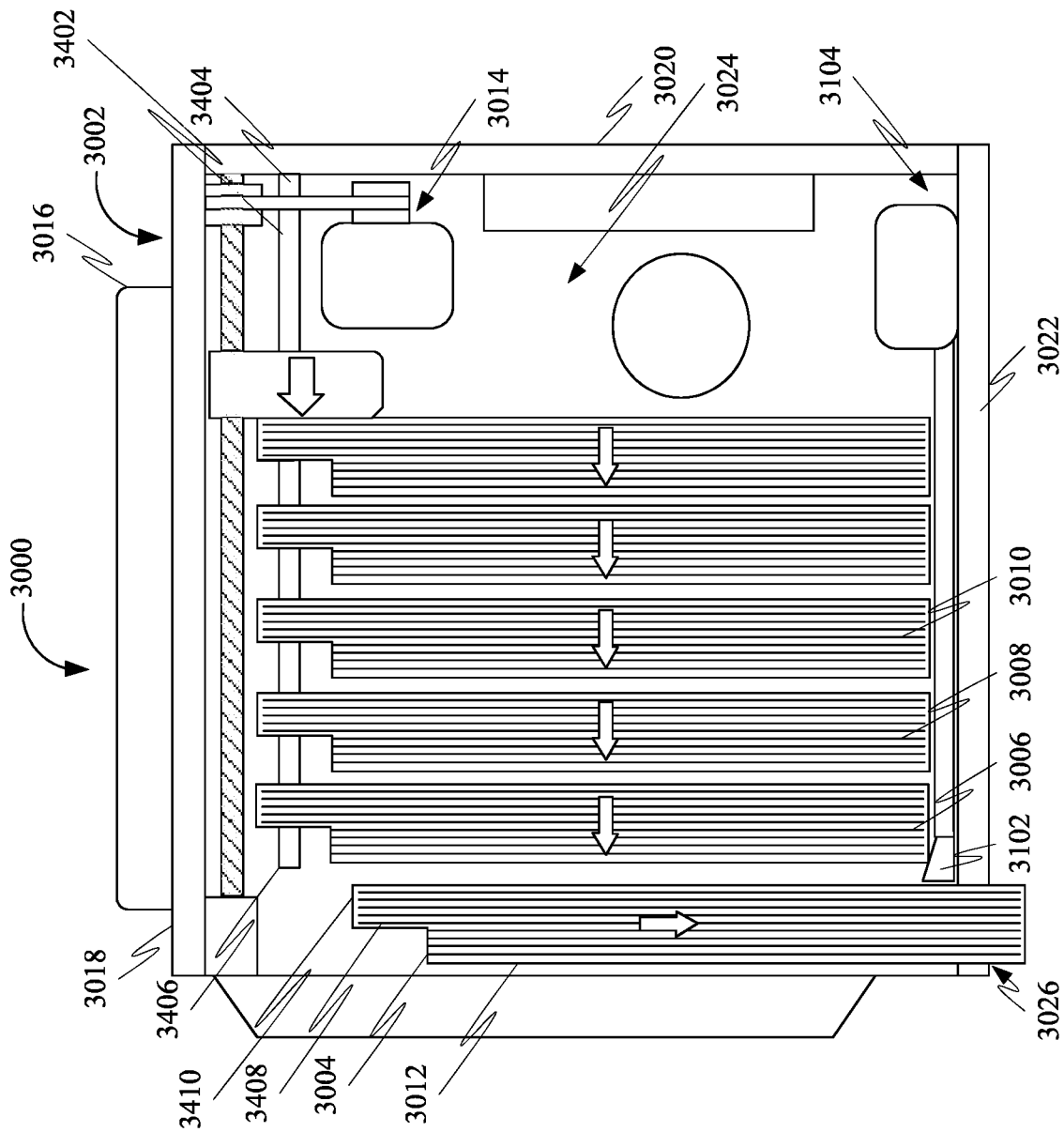
FIG. 34 is a side cross-sectional view of the apparatus, in accordance with some embodiments.

Further, in some embodiments, the apparatus body 3002 may include at least one rod 3402, as shown in FIG. 34. Further, the at least one rod 3402 may include a first end 3404 and a second end 3406. Further, the first end 3402 of the at least one rod 3402 may be attached to a first body wall of the at least one body wall 3018-3022 and the second end 3406 extends away from the first body wall in the at least one body interior space 3024. Further, the at least one bottomless tray 3004-3010 may include at least one recess 3408, as shown in FIG. 34, comprised in a top end 3410, as shown in FIG. 34, of the at least one bottomless tray 3004-3010 for removably receiving the at least one rod 3402. Further, the at least one bottomless tray 3004-3010 may be removably inserted into the at least one rod 3402 through the second end 3406 based on the removably receiving. Further, the at least one bottomless tray 3004-3010 may be held onto the at least one rod 3402 in the at least one storage position based on inserting of the at least one rod 3402 into the at least one recess 3408. Further, the at least one bottomless tray 3004-3010 may be released from the at least one rod 3402 in the dispensing position based on removing of the at least one rod 3402 from the at least one recess 3408.

Figure 35:
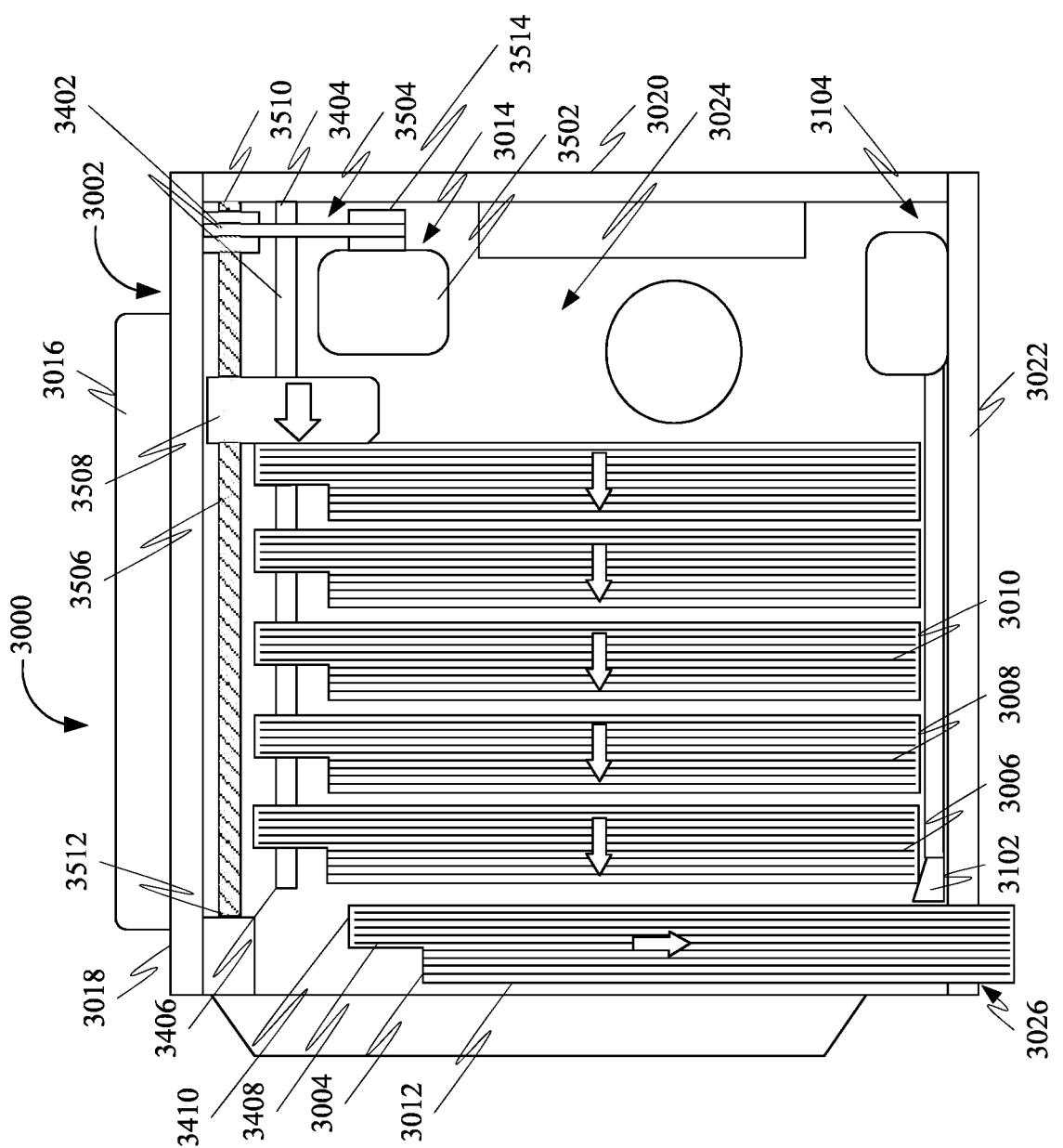
FIG. 35 is a side cross-sectional view of the apparatus, in accordance with some embodiments.

Further, in an embodiment, the at least one refilling actuator 3014 may include a first motor 3502, as shown in FIG. 35. Further, the first motor 3502 may be coupled with the at least one bottomless tray 3004-3010 using at least one refilling assembly 3504, as shown in FIG. 35. Further, the at least one refilling assembly 3504 may include a first threaded rod 3506 and a first pusher 3508, as shown in FIG. 35. Further, the first threaded rod 3506 may include a first end 3510 and a second end 3512, as shown in FIG. 35. Further, the first end 3510 of the first threaded rod 3506 may be mechanically coupled with a shaft 3514, as shown in FIG. 35, of the first motor 3502. Further, the first pusher 3508 may include a threaded recess threadedly coupled with the first threaded rod 3506. Further, the first motor 3502 may be configured for rotating the first threaded rod 3506. Further, the first pusher 3508 may be configured for moving along the first threaded rod 3506 between the first end 3510 of the first threaded rod 3506 and the second end 3512 of the first threaded rod 3506 based on the rotating of the first threaded rod 3506. Further, the displacing of the at least one bottomless tray 3004-3010 from the at least one storage position to the dispensing position may be based on the moving of the first pusher 3508.

In further embodiments, the apparatus 3000 may include at least one dispensing actuator coupled with the at least one bottomless tray 3004-3010. Further, the at least one dispensing actuator may be configured for moving the at least one bottomless tray 3004-3010 in the dispensing position out of the apparatus body 3002 through the at least one body opening 3026. Further, the at least one power source 3016 may be coupled with the at least one dispensing actuator.

Further, the at least one power source 3016 may be configured for powering the at least one dispensing actuator.

Further, in an embodiment, the at least one dispensing actuator may include a second motor. Further, the second motor may be coupled with the at least one bottomless tray 3004-3010 using at least one dispensing assembly. Further, the at least one dispensing assembly may include a second threaded rod and a second pusher. Further, the second threaded rod may include a first end and a second end. Further, the first end of the second threaded rod may be mechanically coupled with a shaft of the second motor. Further, the second pusher may include a threaded recess threadedly coupled with the second threaded rod. Further, the second motor may be configured for rotating the second threaded rod. Further, the second pusher may be configured for moving along the second threaded rod between the first end of the second threaded rod and the second end of the second threaded rod based on the rotating of the second threaded rod. Further, the moving of the at least one bottomless tray 3004-3010 in the dispensing position out of the apparatus body 3002 through the at least one body opening 3026 may be based on the moving of the second pusher along the second threaded rod. Further, in an embodiment, the at least one refilling actuator 3014 may include a third motor. Further, the third motor may be coupled with the at least one bottomless tray 3004-3010 using at least one first dispensing assembly. Further, the at least one first dispensing assembly may include a third threaded rod and a lifter. Further, the third threaded rod may include a first end and a second end. Further, the first end of the third threaded rod may be mechanically coupled with a shaft of the third motor. Further, the lifter may include a threaded recess threadedly coupled with the third threaded rod. Further, the at least one bottomless tray 3004-3010 may be disposed on the lifter. Further, the third motor may be configured for rotating the third threaded rod. Further, the lifter may be configured for moving along the third threaded rod between the first end of the third threaded rod and the second end of the third threaded rod based on the rotating of the third threaded rod. Further, the displacing of the at least one bottomless tray 3004-3010 from the at least one storage position to the dispensing position within the at least one body interior space 3024 may be further based on the moving of the lifter along the third threaded rod.

Further, in an embodiment, the apparatus body 3002 may be removably couplable to the programmable medication dispenser. Further, at least one tray receiving portion of the programmable medication dispenser may be configured to be coupled with the at least one body opening 3026. Further, the second pusher may be configured for inserting the at least one bottomless tray 3004-3010 into the programmable medication dispenser through the at least one tray receiving portion based on the moving of the at least one bottomless tray 3004-3010 in the dispensing position along the threaded rod. Further, the inserting may include the dispensing of the at least one bottomless tray 3004-3010 through the at least one body opening 3026. In further embodiments, the apparatus 3000 may include at least one locking mechanism disposed on the at least one body wall 3018-3022. Further, the at least one locking mechanism may be configured for transitioning between a lock state and an unlock state for unlockably locking the programmable medication dispenser to the apparatus body 3002 after coupling of the at least one tray receiving portion with the at least one body opening 3026. Further, the at least one locking mechanism prevents a relative movement between the programmable medication dispenser and the apparatus body 3002 in the lock state. Further, the at least one locking mechanism allows the relative movement between the programmable medication dispenser and the apparatus body 3002 in the unlock state.

Figure 36:
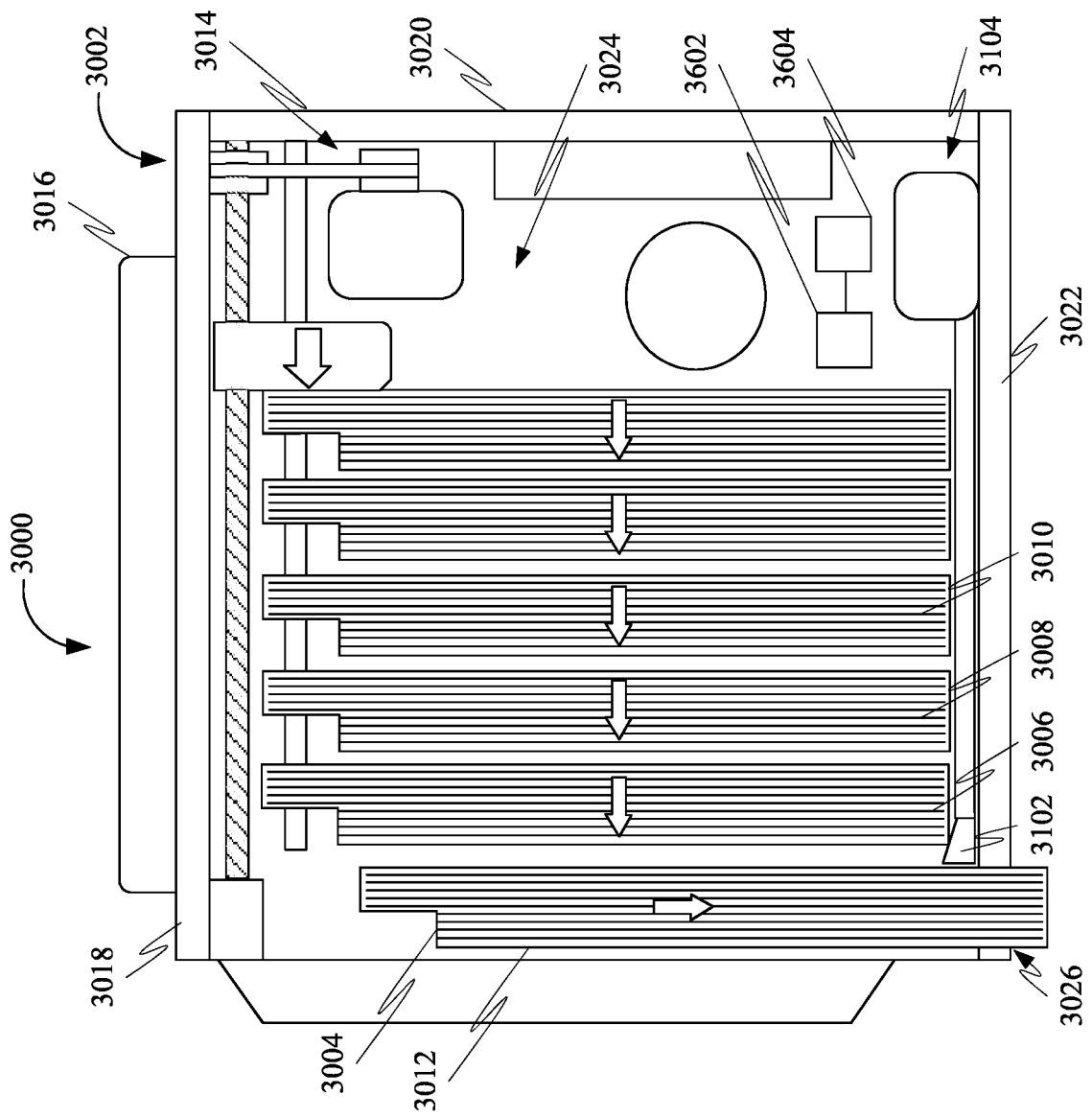
FIG. 36 is a side cross-sectional view of the apparatus, in accordance with some embodiments.

In further embodiments, the apparatus 3000 may include a communication device 3602 and a processing device 3604, as shown in FIG. 36. Further, the communication device 3602 may be disposed on the apparatus body 3002. Further, the communication device 3602 may be configured for receiving at least one prescription of the at least one medication from a storage device of the programmable medication dispenser. Further, the storage device stores at least one data. Further, the at least one data may include the at least one prescription of the at least one medication. Further, the communication device 3602 may be configured for receiving at least one additional information from at least one external device. Further, the at least one additional information may include a current date, a current time, etc. Further, the processing device 3604 may be disposed on the apparatus body 3002. Further, the processing device 3604 may be communicatively coupled with the communication device 3602. Further, the processing device 3604 may be configured for analyzing the at least one prescription and the at least one additional information. Further, the processing device 3604 may be configured for determining at least one dispensing condition for the dispensing of the at least one bottomless tray 3004-3010 based on the analyzing. Further, the processing device 3604 may be configured for generating at least one dispensing command for the dispensing of the at least one bottomless tray 3004-3010 based on the determining. Further, the processing device 3604 may be communicatively coupled with the at least one refilling actuator 3014. Further, the dispensing of the at least one bottomless tray 3004-3010 may be based on the at least one dispensing command.

Figure 37:
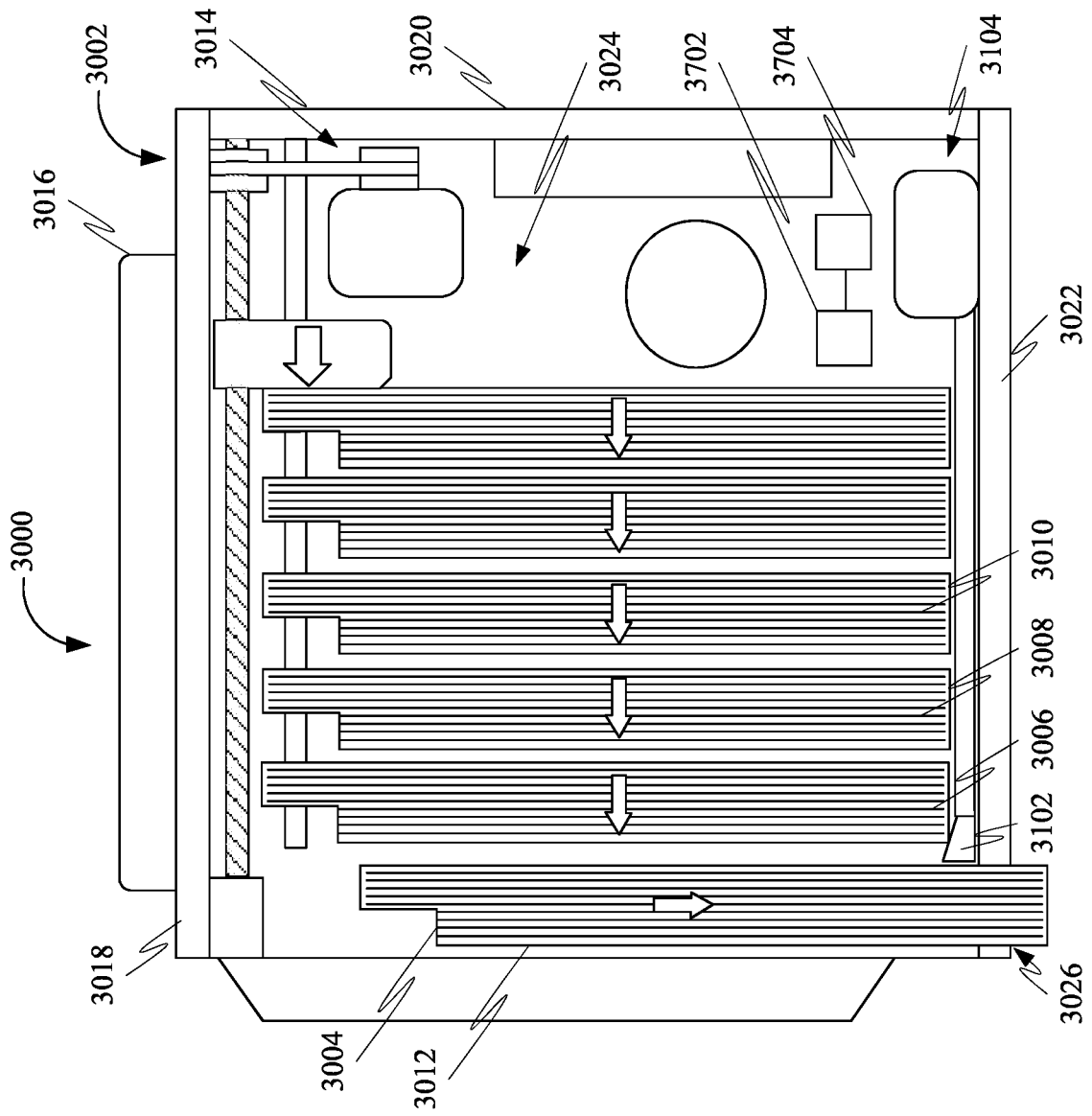
FIG. 37 is a side cross-sectional view of the apparatus, in accordance with some embodiments.

In further embodiments, the apparatus 3000 may include at least one second sensor 3702 and a processing device 3704, as shown in FIG. 37. Further, the at least one second sensor 3702 may be associated with the programmable medication dispenser. Further, the at least one second sensor 3702 may be configured for generating at least one second sensor data based on a quantity of at least one medication present in the programmable medication dispenser. Further, the processing device 3704 may be disposed on the apparatus body 3002. Further, the processing device 3704 may be communicatively coupled with the at least one second sensor 3702. Further, the processing device 3704 may be configured for analyzing the at least one second sensor data. Further, the processing device 3704 may be configured for determining at least one dispensing condition for the dispensing of the at least one bottomless tray 3004-3010 based on the analyzing. Further, the processing device 3704 may be configured for generating at least one dispensing command for the dispensing of the at least one bottomless tray 3004-3010 based on the determining. Further, the processing device 3704 may be communicatively coupled with the at least one refilling actuator 3014. Further, the dispensing of the at least one bottomless tray 3004-3010 may be based on the at least one dispensing command.

Figure 38:
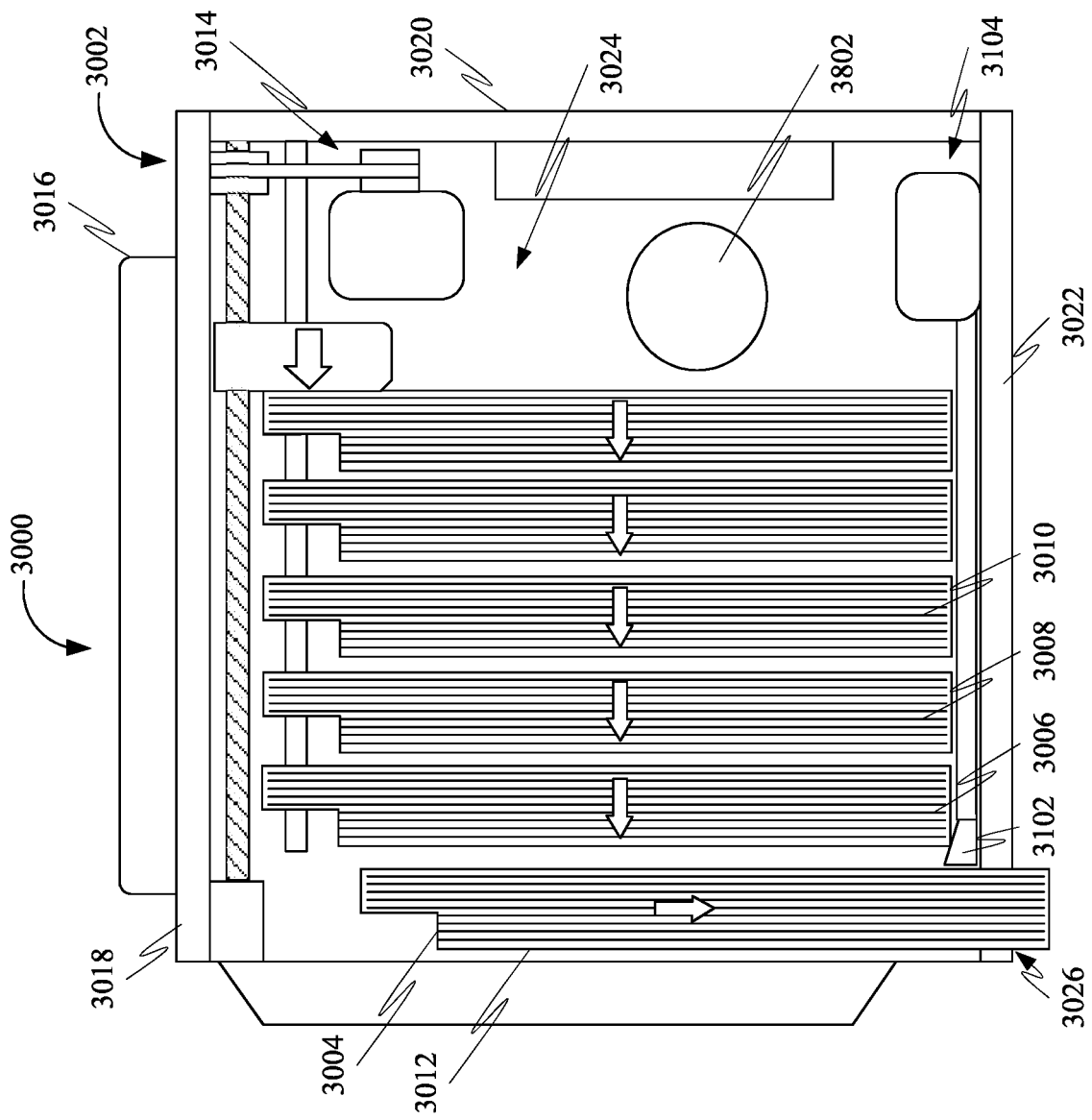
FIG. 38 is a side cross-sectional view of the apparatus, in accordance with some embodiments.

In further embodiments, the apparatus 3000 may include a dehumidifier 3802, as shown in FIG. 38, disposed in the at least one body interior space 3024. Further, the dehumidifier 3802 may be configured for absorbing at least an amount of moisture from air associated with the at least one body interior space 3024.

FIG. 31 is a side cross-sectional view of the apparatus 3000, in accordance with some embodiments.

FIG. 32 is a side cross-sectional view of the apparatus 3000, in accordance with some embodiments.

FIG. 33 is a side cross-sectional view of the apparatus 3000, in accordance with some embodiments.

FIG. 34 is a side cross-sectional view of the apparatus 3000, in accordance with some embodiments.

FIG. 35 is a side cross-sectional view of the apparatus 3000, in accordance with some embodiments.

FIG. 36 is a side cross-sectional view of the apparatus 3000, in accordance with some embodiments.

FIG. 37 is a side cross-sectional view of the apparatus 3000, in accordance with some embodiments.

FIG. 38 is a side cross-sectional view of the apparatus 3000, in accordance with some embodiments.

Figure 39:
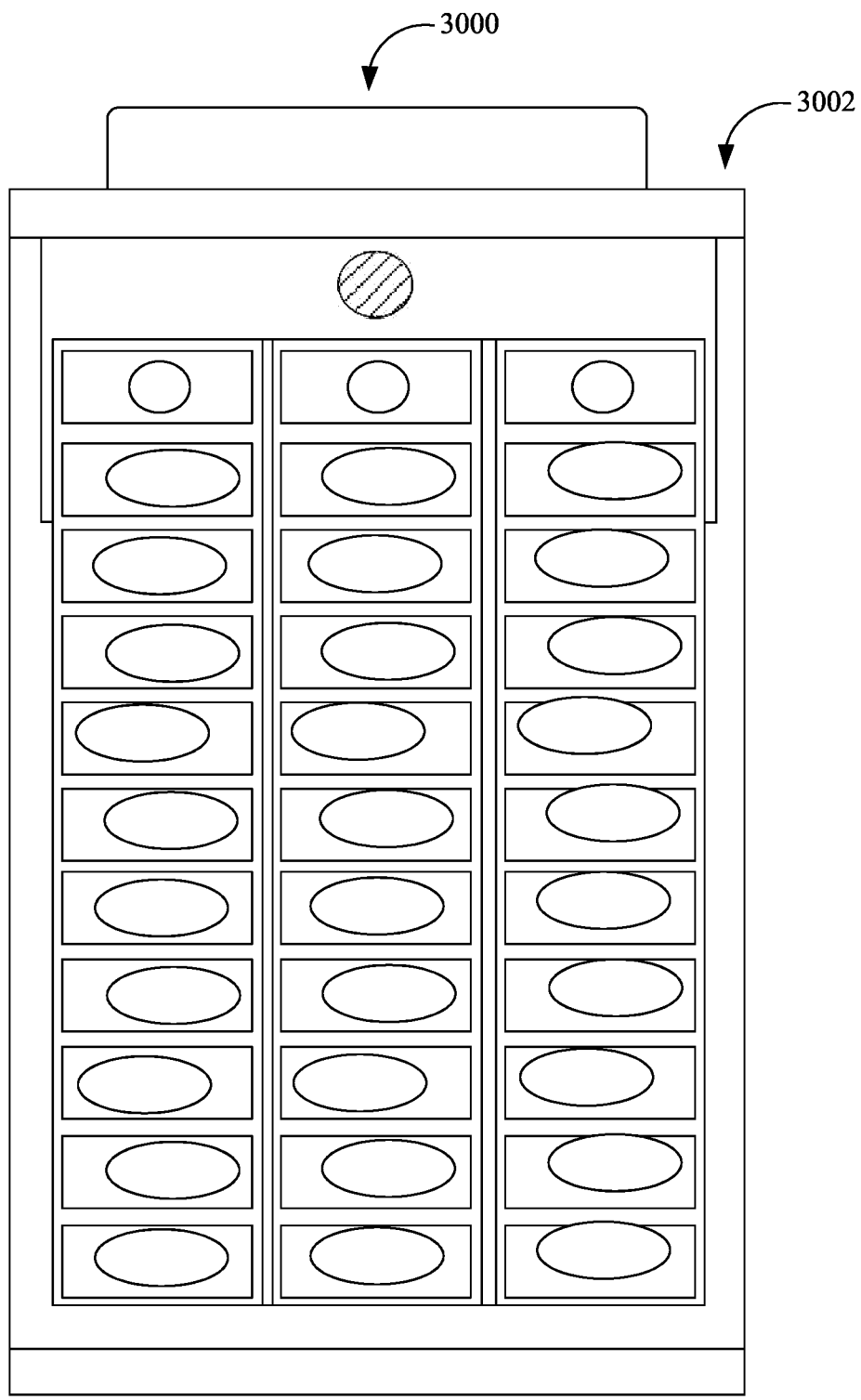
FIG. 39 is a front cross-sectional view of the apparatus, in accordance with some embodiments.

FIG. 39 is a front cross-sectional view of the apparatus 3000, in accordance with some embodiments.

Figure 40:
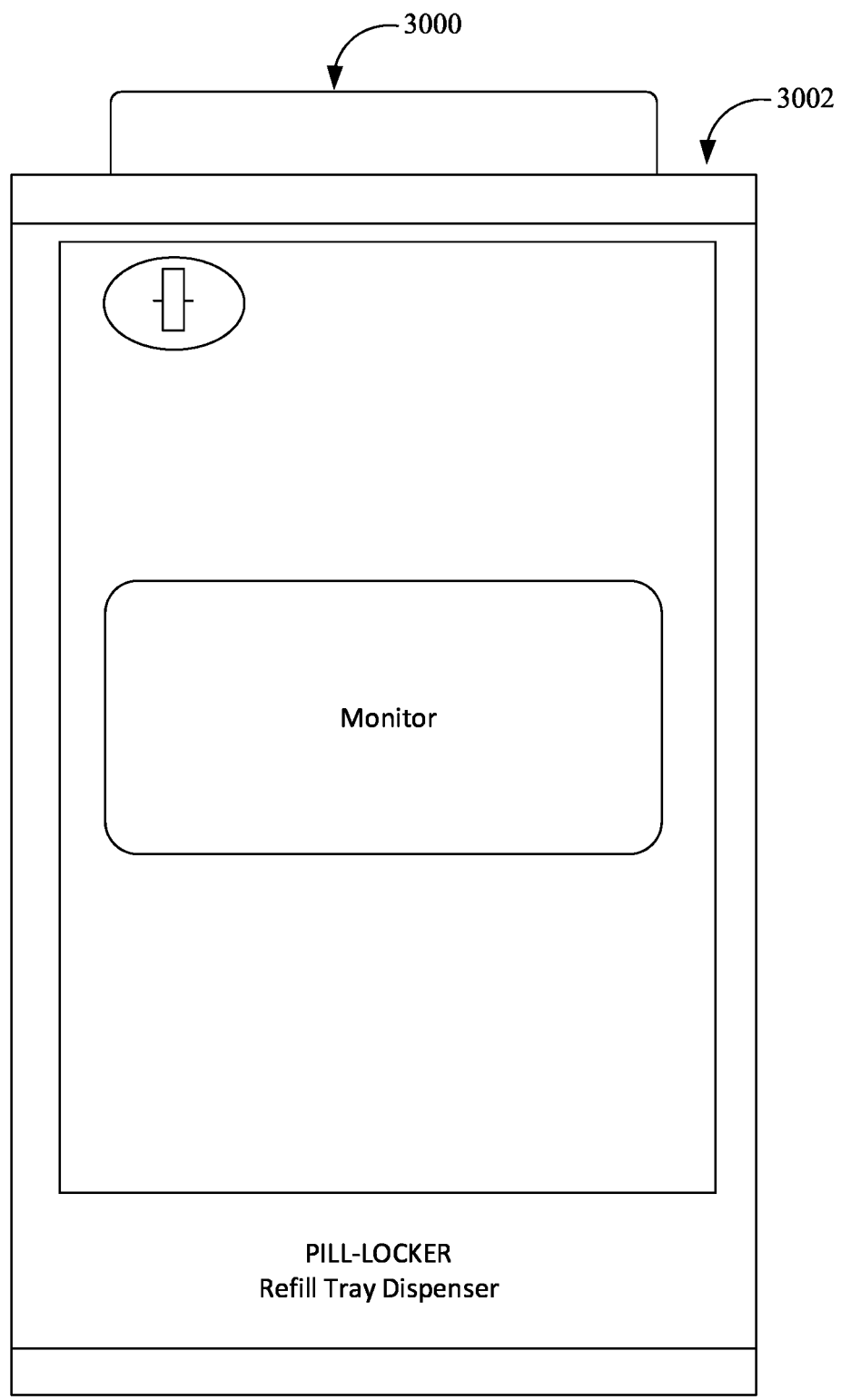
FIG. 40 is a front view of the apparatus, in accordance with some embodiments.

FIG. 40 is a front view of the apparatus 3000, in accordance with some embodiments.

Figure 41:
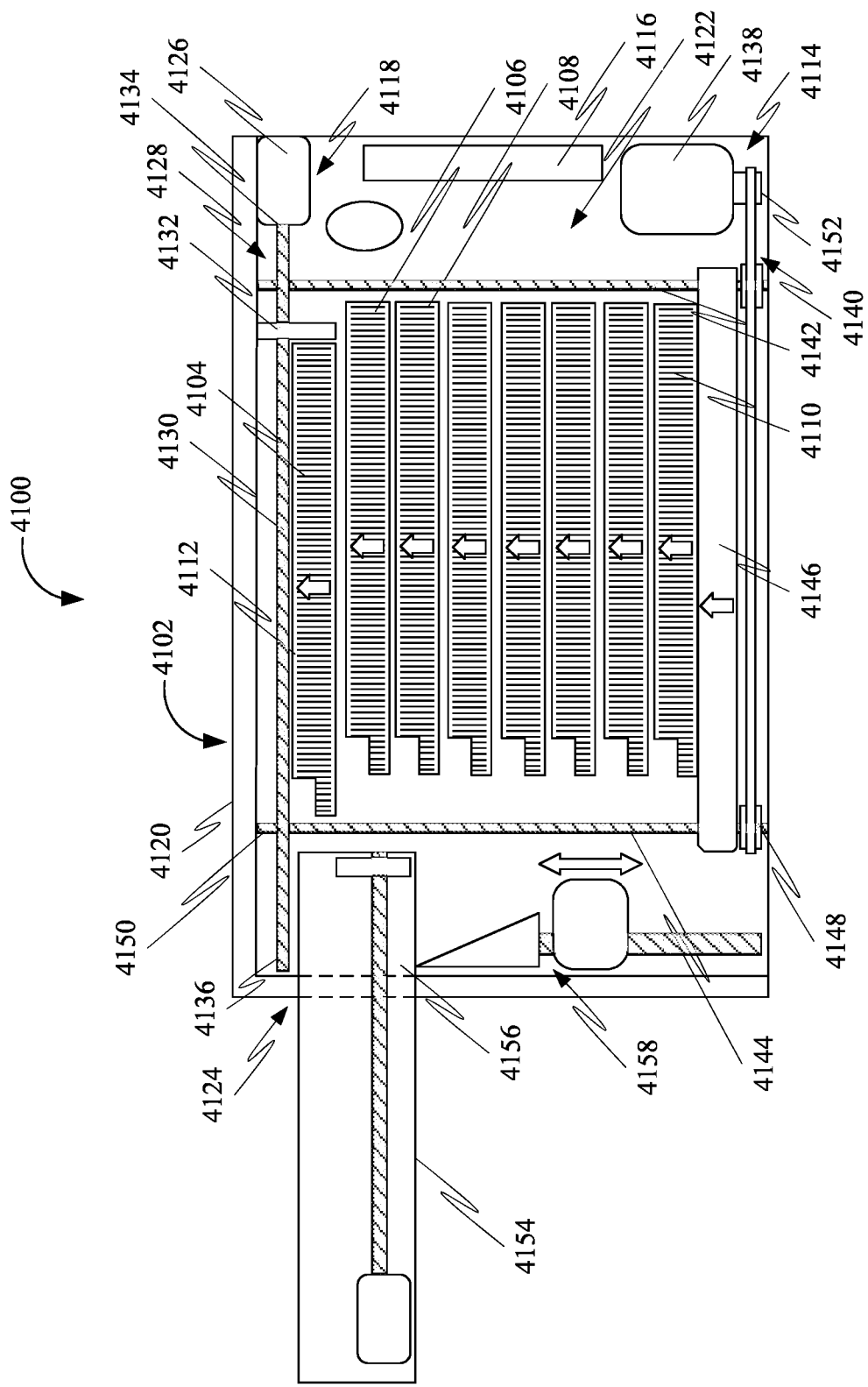
FIG. 41 is a side cross-sectional view of an apparatus for facilitating refilling of medication into a programmable medication dispenser, in accordance with some embodiments.

FIG. 41 is a side cross-sectional view of an apparatus 4100 for facilitating refilling of medication into a programmable medication dispenser 4154, in accordance with some embodiments. Further, the apparatus 4100 may include an apparatus body 4102, at least one bottomless tray 4104-4110, at least one cover 4112, at least one refilling actuator 4114, at least one power source 4116, and at least one dispensing actuator 4118.

Further, the apparatus body 4102 may include at least one body wall 4120 and at least one body interior space 4122 formed by the at least one body wall 4120. Further, the at least one body wall 4120 may include at least one body opening leading 4124 into the at least one body interior space 4122.

Further, the at least one bottomless tray 4104-4110 may be configured to be movably disposed within the at least one body interior space 4122. Further, the at least one bottomless tray 4104-4110 may include a plurality of compartments. Further, each compartment of the plurality of compartments may include at least one compartment opening and at least one compartment wall forming a corresponding compartment. Further, the plurality of compartments may include at least one medication.

Further, the at least one cover 4112 may be removably attached to at least one side of the at least one bottomless tray 4104-4110 for securing the at least one medication in the plurality of compartments.

Further, the at least one refilling actuator 4114 may be coupled with the at least one bottomless tray 4104-4110. Further, the at least one refilling actuator 4114 may be configured for displacing the at least one bottomless tray 4104-4110 from at least one storage position to a dispensing position within the at least one body interior space 4122. Further, the at least one bottomless tray 4104-4110 may be dispensable through the at least one body opening 4124 in the dispensing position. Further, the at least one bottomless tray 4104-4110 may not be dispensable through the at least one body opening 4124 in the at least one storage position. Further, the programmable medication dispenser 4154 receives the at least one bottomless tray 4104-4110 through the at least one body opening 4124 based on dispensing of the at least one bottomless tray 4104-4110 through the at least one body opening 4124.

Further, at least one power source 4116 may be coupled with the at least one refilling actuator 4114. Further, the at least one power source 4116 may be configured for powering the at least one refilling actuator 4114.

Further, the at least one dispensing actuator 4118 may be coupled with the at least one bottomless tray 4104-4110. Further, the at least one dispensing actuator 4118 may be configured for moving the at least one bottomless tray 4104-4110 in the dispensing position out of the apparatus body 4102 through the at least one body opening 4124. Further, the at least one power source 4116 may be coupled with the at least one dispensing actuator 4118. Further, the at least one power source 4116 may be configured for powering the at least one dispensing actuator 4118.

Further, in some embodiments, the at least one dispensing actuator 4118 may include a second motor 4126. Further, the second motor 4126 may be coupled with the at least one bottomless tray 4104-4110 using at least one dispensing assembly 4128. Further, the at least one dispensing assembly 4128 may include a second threaded rod 4130 and a second pusher 4132. Further, the second threaded rod 4130 may include a first end 4134 and a second end 4136. Further, the first end 4134 of the second threaded rod 4130 may be mechanically coupled with a shaft of the second motor 4126. Further, the second pusher 4132 may include a threaded recess threadedly coupled with the second threaded rod 4130. Further, the second motor 4126 may be configured for rotating the second threaded rod 4130. Further, the second pusher 4132 may be configured for moving along the second threaded rod 4130 between the first end 4134 of the second threaded rod 4130 and the second end 4136 of the second threaded rod 4130 based on the rotating of the second threaded rod 4130. Further, the moving of the at least one bottomless tray 4104-4110 in the dispensing position out of the apparatus body 4102 through the at least one body opening 4124 may be based on the moving of the second pusher 4132 along the second threaded rod 4130.

Further, in an embodiment, the at least one refilling actuator 4114 may include a third motor 4138. Further, the third motor 4138 may be coupled with the at least one bottomless tray 4104-4110 using at least one first dispensing assembly 4140. Further, the at least one first dispensing assembly 4140 may include a third threaded rod 4142-4144 and a lifter 4146. Further, the third threaded rod 4142-4144 may include a first end 4148 and a second end 4150. Further, the first end 4148 of the third threaded rod 4142-4144 may be mechanically coupled with a shaft 4152 of the third motor 4138. Further, the lifter 4146 may include a threaded recess threadedly coupled with the third threaded rod 4142-4144. Further, the at least one bottomless tray 4104-4110 may be disposed on the lifter 4146. Further, the third motor 4138 may be configured for rotating the third threaded rod 4142-4144. Further, the lifter 4146 may be configured for moving along the third threaded rod 4142-4144 between the first end 4148 of the third threaded rod 4142-4144 and the second end 4150 of the third threaded rod 4142-4144 based on the rotating of the third threaded rod 4142-4144. Further, the displacing of the at least one bottomless tray 4104-4110 from the at least one storage position to the dispensing position within the at least one body interior space 4122 may be further based on the moving of the lifter 4146 along the third threaded rod 4142-4144.

Further, in some embodiments, the apparatus body 4102 may be removably couplable to the programmable medication dispenser 4154. Further, at least one tray receiving portion 4156 of the programmable medication dispenser 4154 may be configured to be coupled with the at least one body opening 4124. Further, the second pusher 4132 may be configured for inserting the at least one bottomless tray 4104-4110 into the programmable medication dispenser 4154 through the at least one tray receiving portion 4156 based on the moving of the at least one bottomless tray 4104-4110 in the dispensing position along the threaded rod.

Further, the inserting may include the dispensing of the at least one bottomless tray 4104-4110 through the at least one body opening 4124. In further embodiments, the apparatus 4100 may include at least one locking mechanism 4158 disposed on the at least one body wall 4120. Further, the at least one locking mechanism 4158 may be configured for transitioning between a lock state and an unlock state for unlockably locking the programmable medication dispenser 4154 to the apparatus body 4102 after coupling of the at least one tray receiving portion 4156 with the at least one body opening 4124. Further, the at least one locking mechanism 4158 prevents a relative movement between the programmable medication dispenser 4154 and the apparatus body 4102 in the lock state. Further, the at least one locking mechanism 4158 allows the relative movement between the programmable medication dispenser 4154 and the apparatus body 4102 in the unlock state.

Although the present disclosure has been explained in relation to its preferred embodiment, it is to be understood that many other possible modifications and variations can be made without departing from the spirit and scope of the disclosure.

The following is claimed:

1. An apparatus for facilitating refilling of medication into a programmable medication dispenser, the apparatus comprising:
    an apparatus body comprising at least one body wall and at least one body interior space formed by the at least one body wall, wherein the at least one body wall comprises at least one body opening leading into the at least one body interior space;
    at least one bottomless tray configured to be movably disposed within the at least one body interior space, wherein the at least one bottomless tray comprises a plurality of compartments, wherein each compartment of the plurality of compartments comprises at least one compartment opening and at least one compartment wall forming a corresponding compartment, wherein the plurality of compartments comprises at least one medication;
    at least one cover removably attached to at least one side of the at least one bottomless tray for securing the at least one medication in the plurality of compartments;
    at least one refilling actuator coupled with the at least one bottomless tray, wherein the at least one refilling actuator is configured for displacing the at least one bottomless tray from at least one storage position to a dispensing position within the at least one body interior space, wherein the at least one bottomless tray is dispensable through the at least one body opening in the dispensing position, wherein the at least one bottomless tray is not dispensable through the at least one body opening in the at least one storage position, wherein the programmable medication dispenser receives the at least one bottomless tray through the at least one body opening based on dispensing of the at least one bottomless tray through the at least one body opening;
    at least one power source coupled with the at least one refilling actuator, wherein the at least one power source is configured for powering the at least one refilling actuator; and
    the apparatus body further comprising at least one rod, wherein the at least one rod comprises a first end and a second end, wherein the first end of the at least one rod is attached to a first body wall of the at least one body wall and the second end extends away from the first body wall in the at least one body interior space, wherein the at least one bottomless tray comprises at least one recess comprised in a top end of the at least one bottomless tray for removably receiving the at least one rod, wherein the at least one bottomless tray is removably inserted into the at least one rod through the second end based on the removably receiving, wherein the at least one bottomless tray is held onto the at least one rod in the at least one storage position based on inserting of the at least one rod into the at least one recess, wherein the at least one bottomless tray is released from the at least one rod in the dispensing position based on removing of the at least one rod from the at least one recess.

2. The apparatus of claim 1 further comprising at least one lid coupled with the at least one body opening, wherein the at least one lid is configured for transitioning between an open state and a closed state, wherein the at least one lid covers the at least body opening for preventing the dispensing of the at least one bottomless tray through the at least one body opening in the closed state, wherein the at least one lid does not cover the at least one body opening for allowing the dispensing of the at least one bottomless tray through the at least one body opening in the open state.

3. The apparatus of claim 2 further comprising at least one lid actuator coupled with the at least one lid, wherein the at least one lid actuator is configured for displacing the at least one lid between an open position and a closed position for the transitioning of the at least one lid, wherein the open position corresponds to the open state and the closed position corresponds to the closed state, wherein the at least one power source is further coupled with the at least one lid actuator, wherein the at least one power source is further configured for powering the at least one lid actuator.

4. The apparatus of claim 3 further comprising:
    at least one first sensor disposed in the at least one body interior space, wherein the at least one first sensor is configured for generating at least one first sensor data based on a position of the at least one bottomless tray in relation to the at least one body opening; and
    a processing device disposed on the apparatus body, wherein the processing device is communicatively coupled with the at least one first sensor, wherein the processing device is configured for:
        analyzing the at least one first sensor data;
        determining a dispensing state of the at least bottomless tray based on the analyzing; and
        generating at least one lid control command based on the determining, wherein the processing device is communicatively coupled with the at least one lid actuator, wherein the displacing of the at least one lid between the open position and the closed position is based on the at least one lid control command.

5. The apparatus of claim 1 further comprising:
    at least one sensor disposed in the at least one body interior space, wherein the at least one sensor is configured for generating at least one sensor data based on at least one of a relative position and a relative orientation of the at least one bottomless tray in relation to the at least one body opening; and
    a processing device disposed on the apparatus body, wherein the processing device is communicatively coupled with the at least one sensor, wherein the processing device is configured for:

analyzing the at least one sensor data;
determining at least one displacement condition for the displacing of the at least one bottomless tray based on the analyzing; and
generating at least one displacement command for the displacing of the at least one bottomless tray based on the determining, wherein the processing device is communicatively coupled with the at least one refilling actuator, wherein the displacing of the at least one bottomless tray is further based on the at least one displacement command.

6. The apparatus of claim 1, wherein the at least one refilling actuator comprises a first motor, wherein the first motor is coupled with the at least one bottomless tray using at least one refilling assembly, wherein the at least one refilling assembly comprises a first threaded rod and a first pusher, wherein the first threaded rod comprises a first end and a second end, wherein the first end of the first threaded rod is mechanically coupled with a shaft of the first motor, wherein the first pusher comprises a threaded recess threadedly coupled with the first threaded rod, wherein the first motor is configured for rotating the first threaded rod, wherein the first pusher is configured for moving along the first threaded rod between the first end of the first threaded rod and the second end of the first threaded rod based on the rotating of the first threaded rod, wherein the displacing of the at least one bottomless tray from the at least one storage position to the dispensing position is based on the moving of the first pusher.

7. The apparatus of claim 1 further comprising at least one dispensing actuator coupled with the at least one bottomless tray, wherein the at least one dispensing actuator is configured for moving the at least one bottomless tray in the dispensing position out of the apparatus body through the at least one body opening, wherein the at least one power source is further coupled with the at least one dispensing actuator, wherein the at least one power source is further configured for powering the at least one dispensing actuator.

8. The apparatus of claim 7, wherein the at least one dispensing actuator comprises a second motor, wherein the second motor is coupled with the at least one bottomless tray using at least one dispensing assembly, wherein the at least one dispensing assembly comprises a second threaded rod and a second pusher, wherein the second threaded rod comprises a first end and a second end, wherein the first end of the second threaded rod is mechanically coupled with a shaft of the second motor, wherein the second pusher comprises a threaded recess threadedly coupled with the second threaded rod, wherein the second motor is configured for rotating the second threaded rod, wherein the second pusher is configured for moving along the second threaded rod between the first end of the second threaded rod and the second end of the second threaded rod based on the rotating of the second threaded rod, wherein the moving of the at least one bottomless tray in the dispensing position out of the apparatus body through the at least one body opening is based on the moving of the second pusher along the second threaded rod.

9. The apparatus of claim 8, wherein the at least one refilling actuator further comprises a third motor, wherein the third motor is coupled with the at least one bottomless tray using at least one first dispensing assembly, wherein the at least one first dispensing assembly comprises a third threaded rod and a lifter, wherein the third threaded rod comprises a first end and a second end, wherein the first end of the third threaded rod is mechanically coupled with a shaft of the third motor, wherein the lifter comprises a threaded recess threadedly coupled with the third threaded rod, wherein the at least one bottomless tray is disposed on the lifter, wherein the third motor is configured for rotating the third threaded rod, wherein the lifter is configured for moving along the third threaded rod between the first end of the third threaded rod and the second end of the third threaded rod based on the rotating of the third threaded rod, wherein the displacing of the at least one bottomless tray from the at least one storage position to the dispensing position within the at least one body interior space is further based on the moving of the lifter along the third threaded rod.

10. The apparatus of claim 8, wherein the apparatus body is removably couplable to the programmable medication dispenser, wherein at least one tray receiving portion of the programmable medication dispenser is configured to be coupled with the at least one body opening, wherein the second pusher is configured for inserting the at least one bottomless tray into the programmable medication dispenser through the at least one tray receiving portion based on the moving of the at least one bottomless tray in the dispensing position along the threaded rod, wherein the inserting comprises the dispensing of the at least one bottomless tray through the at least one body opening.

11. The apparatus of claim 10 further comprising at least one locking mechanism disposed on the at least one body wall, wherein the at least one locking mechanism is configured for transitioning between a lock state and an unlock state for unlockably locking the programmable medication dispenser to the apparatus body after coupling of the at least one tray receiving portion with the at least one body opening, wherein the at least one locking mechanism prevents a relative movement between the programmable medication dispenser and the apparatus body in the lock state, wherein the at least one locking mechanism allows the relative movement between the programmable medication dispenser and the apparatus body in the unlock state.

12. The apparatus of claim 1 further comprising:
a communication device disposed on the apparatus body, wherein the communication device is configured for:
receiving at least one prescription of the at least one medication from a storage device of the programmable medication dispenser, wherein the storage device stores at least one data, wherein the at least one data comprises the at least one prescription of the at least one medication; and
receiving at least one additional information from at least one external device; and
a processing device disposed on the apparatus body, wherein the processing device is communicatively coupled with the communication device, wherein the processing device is configured for:
analyzing the at least one prescription and the at least one additional information;
determining at least one dispensing condition for the dispensing of the at least one bottomless tray based on the analyzing; and
generating at least one dispensing command for the dispensing of the at least one bottomless tray based on the determining, wherein the processing device is communicatively coupled with the at least one refilling actuator, wherein the dispensing of the at least one bottomless tray is further based on the at least one dispensing command.

13. The apparatus of claim 1 further comprising:
at least one second sensor associated with the programmable medication dispenser, wherein the at least one second sensor is configured for generating at least one second sensor data based on a quantity of at least one medication present in the programmable medication dispenser; and a processing device disposed on the apparatus body, wherein the processing device is communicatively coupled with the at least one second sensor, wherein the processing device is configured for:
analyzing the at least one second sensor data;
determining at least one dispensing condition for the dispensing of the at least one bottomless tray based on the analyzing; and
generating at least one dispensing command for the dispensing of the at least one bottomless tray based on the determining, wherein the processing device is communicatively coupled with the at least one refilling actuator, wherein the dispensing of the at least one bottomless tray is further based on the at least one dispensing command.

14. The apparatus of claim 1 further comprising a dehumidifier disposed in the at least one body interior space, wherein the dehumidifier is configured for absorbing at least an amount of moisture from air associated with the at least one body interior space.

15. An apparatus for facilitating refilling of medication into a programmable medication dispenser, the apparatus comprising:
an apparatus body comprising at least one body wall and at least one body interior space formed by the at least one body wall, wherein the at least one body wall comprises at least one body opening leading into the at least one body interior space;
at least one bottomless tray configured to be movably disposed within the at least one body interior space, wherein the at least one bottomless tray comprises a plurality of compartments, wherein each compartment of the plurality of compartments comprises at least one compartment opening and at least one compartment wall forming a corresponding compartment, wherein the plurality of compartments comprises at least one medication;
at least one cover removably attached to at least one side of the at least one bottomless tray for securing the at least one medication in the plurality of compartments;
at least one refilling actuator coupled with the at least one bottomless tray, wherein the at least one refilling actuator is configured for displacing the at least one bottomless tray from at least one storage position to a dispensing position within the at least one body interior space, wherein the at least one bottomless tray is dispensable through the at least one body opening in the dispensing position, wherein the at least one bottomless tray is not dispensable through the at least one body opening in the at least one storage position, wherein the programmable medication dispenser receives the at least one bottomless tray through the at least one body opening based on dispensing of the at least one bottomless tray through the at least one body opening;
at least one power source coupled with the at least one refilling actuator, wherein the at least one power source is configured for powering the at least one refilling actuator;
at least one dispensing actuator coupled with the at least one bottomless tray, wherein the at least one dispensing actuator is configured for moving the at least one bottomless tray in the dispensing position out of the apparatus body through the at least one body opening, wherein the at least one power source is further coupled with the at least one dispensing actuator, wherein the at least one power source is further configured for powering the at least one dispensing actuator; and
the at least one dispensing actuator comprising a second motor, wherein the second motor is coupled with the at least one bottomless tray using at least one dispensing assembly, wherein the at least one dispensing assembly comprises a second threaded rod and a second pusher, wherein the second threaded rod comprises a first end and a second end, wherein the first end of the second threaded rod is mechanically coupled with a shaft of the second motor, wherein the second pusher comprises a threaded recess threadedly coupled with the second threaded rod, wherein the second motor is configured for rotating the second threaded rod, wherein the second pusher is configured for moving along the second threaded rod between the first end of the second threaded rod and the second end of the second threaded rod based on the rotating of the second threaded rod, wherein the moving of the at least one bottomless tray in the dispensing position out of the apparatus body through the at least one body opening is based on the moving of the second pusher along the second threaded rod.

16. The apparatus of claimer 15, wherein the at least one refilling actuator further comprises a third motor, wherein the third motor is coupled with the at least one bottomless tray using at least one first dispensing assembly, wherein the at least one first dispensing assembly comprises a third threaded rod and a lifter, wherein the third threaded rod comprises a first end and a second end, wherein the first end of the third threaded rod is mechanically coupled with a shaft of the third motor, wherein the lifter comprises a threaded recess threadedly coupled with the third threaded rod, wherein the at least one bottomless tray is disposed on the lifter, wherein the third motor is configured for rotating the third threaded rod, wherein the lifter is configured for moving along the third threaded rod between the first end of the third threaded rod and the second end of the third threaded rod based on the rotating of the third threaded rod, wherein the displacing of the at least one bottomless tray from the at least one storage position to the dispensing position within the at least one body interior space is further based on the moving of the lifter along the third threaded rod.

17. The apparatus of claimer 15, wherein the apparatus body is removably couplable to the programmable medication dispenser, wherein at least one tray receiving portion of the programmable medication dispenser is configured to be coupled with the at least one body opening, wherein the second pusher is configured for inserting the at least one bottomless tray into the programmable medication dispenser through the at least one tray receiving portion based on the moving of the at least one bottomless tray in the dispensing position along the threaded rod, wherein the inserting comprises the dispensing of the at least one bottomless tray through the at least one body opening.

18. The apparatus of claim 17 further comprising at least one locking mechanism disposed on the at least one body wall, wherein the at least one locking mechanism is configured for transitioning between a lock state and an unlock state for unlockably locking the programmable medication dispenser to the apparatus body after coupling of the at least one tray receiving portion with the at least one body opening, wherein the at least one locking mechanism prevents a relative movement between the programmable medication dispenser and the apparatus body in the lock state, wherein the at least one locking mechanism allows the relative movement between the programmable medication dispenser and the apparatus body in the unlock state.

\* \* \* \* \*